(12) United States Patent
Garti et al.

(10) Patent No.: US 11,819,490 B2
(45) Date of Patent: *Nov. 21, 2023

(54) DILUTABLE FORMULATIONS OF CANNABINOIDS AND PROCESSES FOR THEIR PREPARATION

(71) Applicant: Yissum Research Development Company of the Hebrew University of Jerusalem Ltd., Jerusalem (IL)

(72) Inventors: Nissim Garti, Ramat HaSharon (IL); Sharon Garti Levi, Modi'in (IL); Rotem Edri, Eilat (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/338,273

(22) PCT Filed: Sep. 28, 2017

(86) PCT No.: PCT/IL2017/051097
§ 371 (c)(1),
(2) Date: Mar. 29, 2019

(87) PCT Pub. No.: WO2018/061007
PCT Pub. Date: Apr. 5, 2018

(65) Prior Publication Data
US 2019/0314326 A1 Oct. 17, 2019

(30) Foreign Application Priority Data
Sep. 29, 2016 (IL) .......................................... 248149

(51) Int. Cl.
*A61K 31/352* (2006.01)
*A61K 47/10* (2017.01)
(Continued)

(52) U.S. Cl.
CPC .......... *A61K 31/352* (2013.01); *A61K 9/1075* (2013.01); *A61K 9/19* (2013.01);
(Continued)

(58) Field of Classification Search
None
See application file for complete search history.

(56) References Cited

U.S. PATENT DOCUMENTS

2006/0217445 A1    9/2006   Chew et al.
2007/0104741 A1    5/2007   Murty et al.
(Continued)

FOREIGN PATENT DOCUMENTS

CH    706 963 A2    3/2014
CN    1547479 A    11/2004
(Continued)

OTHER PUBLICATIONS

CN103110582A—Google English Translation ([retrieved from on-line website: https://patents.google.com/patent/CN103110582A/en, published in 2013]). (Year: 2013).*

(Continued)

*Primary Examiner* — Kyung S Chang
(74) *Attorney, Agent, or Firm* — XSENSUS LLP

(57) ABSTRACT

Cannabinoid-loaded formulations are characterized by including 0.5 wt. % to 20 wt. % medium chain triglycerides, one or more hydrophilic surfactants, one or more co-surfactants and 0.1 wt. % or more of at least one cannabinoid. The formulations are in microemulsion form, and are fully dilutable by an aqueous diluent.

11 Claims, 22 Drawing Sheets

(51) Int. Cl.
| | |
|---|---|
| A61K 47/14 | (2017.01) |
| A61K 47/24 | (2006.01) |
| A61K 47/26 | (2006.01) |
| A61K 47/32 | (2006.01) |
| A61K 47/44 | (2017.01) |
| A61K 9/107 | (2006.01) |
| A61K 9/19 | (2006.01) |
| A61K 9/48 | (2006.01) |

(52) U.S. Cl.
CPC .......... *A61K 9/4841* (2013.01); *A61K 47/10* (2013.01); *A61K 47/14* (2013.01); *A61K 47/24* (2013.01); *A61K 47/26* (2013.01); *A61K 47/32* (2013.01); *A61K 47/44* (2013.01)

(56) References Cited

U.S. PATENT DOCUMENTS

| | | | |
|---|---|---|---|
| 2008/0279940 | A1 | 11/2008 | Rigassi et al. |
| 2008/0300386 | A1 | 12/2008 | Lazarev et al. |
| 2012/0004319 | A1 | 1/2012 | Shimizu et al. |
| 2013/0089600 | A1 | 4/2013 | Winnicki |
| 2016/0081927 | A1* | 3/2016 | Bromley ............ A61K 2300/00 424/523 |
| 2017/0042808 | A1 | 2/2017 | Hirai et al. |
| 2017/0181940 | A1 | 6/2017 | Richard |
| 2017/0232210 | A1 | 8/2017 | Boeckl et al. |
| 2018/0042845 | A1 | 2/2018 | Sinai et al. |
| 2019/0231833 | A1 | 8/2019 | Garti et al. |

FOREIGN PATENT DOCUMENTS

| | | |
|---|---|---|
| CN | 102145084 A | 8/2011 |
| CN | 103110582 A | 5/2013 |
| CN | 103690580 A | 4/2014 |
| CN | 104619318 A | 5/2015 |
| CN | 105535111 A | 5/2016 |
| CN | 105997985 A | 10/2016 |
| EP | 1155698 A1 | 11/2001 |
| EP | 2 223 913 A1 | 9/2010 |
| IL | 165 528 A | 11/2010 |
| KR | 10-2007-0117578 A | 12/2007 |
| WO | 03/105607 A1 | 12/2003 |
| WO | 2004/056322 A2 | 7/2004 |
| WO | 2006/094829 A1 | 9/2006 |
| WO | 2008/058366 A1 | 5/2008 |
| WO | 2013/044579 A1 | 4/2013 |
| WO | 2013/108254 A1 | 7/2013 |
| WO | 2014/031504 A1 | 2/2014 |
| WO | 2015/011724 A2 | 1/2015 |
| WO | 2016/004410 A1 | 1/2016 |
| WO | 2016/022936 A1 | 2/2016 |
| WO | 2016/064987 A1 | 4/2016 |
| WO | 2018/061007 A1 | 4/2018 |
| WO | 2018/061011 | 4/2018 |

OTHER PUBLICATIONS

Amsalem et al., "Phospholipids-embedded fully dilutable liquid nanostructures. Part 2: The role of sodium diclofenac", Colloids and Surfaces B: Bioterfaces, (2010), vol. 81, No. 2, pp. 422-429.

Database Medline, Lu et al., Apr. 2009. "Study on extraction of quercetin in guava leaf by microemulsion" XP002776489.

Database Medline, Yue et al., May 2014. "Study on extracting and separating curcuminoids from Curcuma longa rhizome using ultrasound strengthen by microemulsion" XP002776488.

Deutch-Kolevzon et al., "Synergistic cosolubilization of omega-3 fatty acid esters and CoQ10 in dilutable microemulsions", Chemistry and Physics of Lipids, (2011), vol. 164, pp. 654-663.

Fisher et al., "Solubilization of simvastatin and phytosterols in a dilutable microemulsion system", Colloids and Sufaces B.: Biointerfaces, (2013), vol. 107, pp. 35-42.

Garti et al., "Nano-sized self assemblies of nonionic surfactants as solubilization reservoirs and microreactors for food systems", Soft Matter Journal, (2005), vol. 1, pp. 206-218.

Lee et al., "Comparison of the Antioxidant and Transmembrane Permeative Activities of the Different Polygonum cuspidatum Extracts in Phospholipid-Based Microemulsions", Journal of Agricultural and Food Chemistry, (2011), vol. 59, pp. 9135-9141.

Liu et al., "A new biocompatible microemulsion increases extraction yield and bioavailability of Andrographis paniculata", Chinese Journal of Natural Medicines, (2016), vol. 14, No. 9, pp. 683-691.

Spernath et al., "Microemulsions as carriers for drugs and nutraceuticals", Adv. in Colloid and Interface Science Journal, (2006), vol. 128, pp. 47-64.

Spernath et al., "Fully dilutable microemulsions embedded with phospholipids and stabilized by short-chain organic acids and polyols", Journal of Colloid and Interface Science, (2006), vol. 299, pp. 900-909.

Spernath et al., "Phase Transition Induced By Water Dilution In Phospholipid U-Tyoe Food-Grade Microemulsions Studied by DSC", Journal of Thermal Analysis and Calorimetry, (2006), vol. 83, Issue 2, pp. 297-308.

Spernath et al., "Phosphatidylcholine embedded microemulsions: Physical properties and improved Caco-2 cell permeability", Journal of Controlled Release, (2007), vol. 119, pp. 279-290.

Vandamme, "Microemulsions as ocular drug delivery systems: recent developments and future challenges", Progress in Retinal and Eye Research, (2002), vol. 21, No. 1, pp. 15-34.

Hua et al.. "Experiment of Extracting Salviae Miltiorrhizae on using O/W Microemulsion", China Journal of Chinese Materia Medica, Nov. 2008, vol. 33, Issue 22, 4 Pages.

Patil et al., "Phytosomes: Increasing Biovailability of Phytoconstituents", Int J of Universal Pharmacy and Bio Sciences, Jul. 2016, vol. 5, No. 4, pp. 81-94.

Veronika Fischer et al., "Toward surfactant-free and water-free microemulsions", Journal of Colloid and Interface Science, vol. 453, 2015, pp. 186-193.

Linh D. Do, et al., "Environmentally Friendly Vegetable Oil Microemulsions Using Extended Surfactants and Linkers", Journal of Surfactants and Detergents, May 2008, 10 pages.

Chodchanok Attaphong, et al., "Phase Behaviors of Vegetable Oil-Based Microemulsion Fuels: The Effects of Temperatures, Surfactants, Oils, and Water in Ethanol", Energy & Fuels, 2013, 8 pages.

\* cited by examiner

DILUTABLE FORMULATIONS OF CANNABINOIDS AND PROCESSES FOR THEIR PREPARATION

TECHNOLOGICAL FIELD

The present disclosure provides cannabinoid-loaded formulations, as well as processes for their preparation.

BACKGROUND ART

References considered to be relevant as background to the presently disclosed subject matter are listed below:
[1] WO 2008/058366
[2] A. Spernath, A. Aserin, *Advances in Colloid and Interface Science* 2006, 128
[3] A. Spernath, A. Aserin, N. Garti, *Journal of Colloid and Interface Science* 2006, 299, 900-909
[4] A. Spernath, A. Aserin, N. Garti, *Journal of Thermal Analysis and calorimetry* 2006, 83
[5] N. Garti, A. Spernath, A. Aserin, R. Lutz, *Soft Matter* 2005, 1
[6] A. Spernath, A. Aserin, L. Ziserman, D. Danino, N. Garti, *Journal of Controlled Release* 2007, 119
[7] WO 03/105607

Acknowledgement of the above references herein is not to be inferred as meaning that these are in any way relevant to the patentability of the presently disclosed subject matter.

BACKGROUND

Cannabinoids have been used for many years in alleviating pain and inflammatory-related syndromes as well as other therapeutic indications (including glaucoma, neuropathic pain, multiple sclerosis, AIDS, fibromyalgia, nausea, and others). The cannabinoids are a family of many active compounds found mainly in the resin-producing pistillate inflorescences of cannabis plants. Although a variety of cannabinoid compounds have been identified in literature thus far, two compounds in particular have been the focus of interest for medicinal uses: tetrahydrocannabinol (THC) and cannabidiol (CBD).

While THC is a psychoactive compound with adverse long-lasting effects on the user, CBD is not identified as a psychotropic agent and is considered safe for consumption in various routes of administration. Both compounds are typically found as a mixture, at various concentration ranges, in the plant source. For formulating into pharmaceutical compositions, the cannabinoids are often extracted from the plant source by various methods, or synthetically manufactured.

One of the methods commonly used is extraction by carrier oils, in which the carrier oil is used as a solvent for the extraction of the cannabinoid species from the plant source. Since the oil-filled trichomes of the inflorescences are fat-soluble, natural plant oils are an effective way to extract the mixture of cannabinoid species from the cannabinoid-laden resin.

Another method often used is extraction by organic solvents, which are selected amongst solvents capable of dissolving cannabinoids. Such extraction requires tailoring of the solvent for effective extraction. However, it is difficult to remove traces of the solvent from the end product, reducing the degree of purity and the safety of the resulting extract.

A further method which is used for obtaining extraction of various compounds from various plant sources is super-critical $CO_2$ extraction. In the $CO_2$ extraction process, $CO_2$ at super-critical conditions (i.e. high temperature and pressure) is used as a solvent for the cannabinoid species. Although very effective for extracting a variety of compounds from the plant source, this technique is often more complicated and expensive compared to liquid extraction.

Although various methods exist for extraction of cannabinoids, these have the common disadvantage of low selectivity. Namely, the extraction methods known to date extract various species of cannabinoids from the plant source, often resulting in a mixture of CBD and THC, hindering the subsequent formulation and use of CBD in pharmaceutical compositions.

The bioavailability of the oral, topical or ophthalmic administered cannabinoids in commercially available products is often found to be poor and insufficient, thereby leading to poor therapeutic effects. There is a need for improved solubility or solubilization, enhanced bioavailability and absorption by a delivery system other than smoking.

GENERAL DESCRIPTION

Solubilization of cannabinoids is provided in the present disclosure by the use of a unique formulation. As further detailed herein, the formulations of this disclosure have the ability to be highly-loaded with various cannabinoids. In addition, the present disclosure provides processes for obtaining such cannabinoid-loaded formulation, as well as various pharmaceutical compositions and administration forms comprising it.

In one of its aspects, this disclosure provides a cannabinoid-loaded formulation comprising at least one oil, at least one hydrophilic surfactant, at least one co-surfactant, and/or one co-solvent and at least 0.1 wt % of a cannabinoid.

The formulations of this disclosure are typically in the form of microemulsions. Microemulsions (MEs) are well-known vehicles for intravenous delivery of drugs because of their spontaneous formation, high solubilization capacity and physical stability [1]. A specific type of microemulsions are spontaneously-formed microemulsions, characterized by a nanoscale droplet size, which are a new and advanced category of delivery vehicles. These microemulsions have been previously studied and their ability to solubilize non-soluble drugs and nutraceuticals has been demonstrated [2-7]. The formulations are self-assembled microemulsion systems of nanodroplets, comprising surfactants and oil. The systems of the present disclosure, as will be explained further herein, comprise at least one oil, at least one hydrophilic surfactant and at least one solvent, and may further comprise additional components such as co-surfactants, co-solvents and phospholipids. In the present disclosure, the term microemulsion(s) will refer to such formulations, unless otherwise defined. The terms "microemulsion" and "formulation" will be used interchangeably.

Formulations of this disclosure may be in the form of substantially water-free (containing up to 10 wt % water) concentrates that can be fully and progressively diluted with aqueous phase to form microemulsions. The concentrated form of the present disclosure, as will be further explained, is fully dilutable with water, contrary to conventional microemulsions known in the art. The diluted formulations (diluted microemulsions) are nano-sized uniform (mono-dispersed) structures, exhibiting zero interfacial tension between the oil phase and the aqueous phase behaving like Newtonian fluids. The formulations are self-assembled upon mixing the surfactants and the oil to form water-free reverse micelles. Upon dilution with water or aqueous solutions, water-swollen micelles or water-in-oil nanodroplets are formed, being able to invert into bicontinuous mesophases in the presence of an aqueous phase, e.g. water. Upon further dilution, they undergo (umbrella type) inversion into oil-in-water droplets.

Without wishing to be bound by theory, these systems are constituted by oil-solvated clusters or short domains of surfactants, however differ from the classical reverse micelles. When mixed with small amounts of aqueous media hydrated and solvated surfactants are formed, and upon further dilution with aqueous phase they are easily transform into oil-in-water (O/W) nanodroplets entrapping into their core the extracted cannabinoid molecules. The transformation to O/W microemulsions is spontaneous, i.e. without the need to employ shearing, mechanical forces or excessive heating conditions. The cannabinoids are entrapped in the core of the reverse micelles and remains at the interface between the oil phase and the aqueous phase upon dilution in the bicontinuous region; thereafter the cannabinoid molecules are located in the core of the droplets once the O/W microemulsion is formed. The interactions (physical complexation) between the cannabinoid and the surfactants (as well as the co-surfactants, when used) allow maintaining the extracted cannabinoid within the oil core throughout the structural transformations of the reverse micelles into a bicontinuous region and finally to the O/W microemulsion, thus stabilizing the formulation and preventing undesired release of the cannabinoid from the oil core prior to its administration (i.e. during storage).

The formulations of this disclosure provide thermodynamically stable microemulsions, with nano-sized droplets, which may be safely stored for prolonged periods of time, without aggregation, coalescence or phase separation. The formulations of the invention are also characterized by a substantially uniform and stable droplets size, typically in the nanometric scale and having a narrow size distribution. The stability of the droplet size is of importance as changes in the droplet size may impair the release of the cannabinoid once administered. Further, the cannabinoid-loaded formulations, when not in diluted form, are substantially devoid of water, and as such do not support (or minimize) microbial growth. Further, due to their high stability and small droplet size, the formulations may be sterilized without the risk of self-contamination in various ways, such as heat sterilization, filtration through a 0.22 um filter, UV and other methods known to the art, without damaging the formulations' beneficial structure.

In the present disclosure, the formulations are designed to solubilize cannabinoids from a variety of sources, such that the cannabinoid-loaded formulation (cannabinoid-loaded microemulsion) is substantially water-free, and can be easily diluted or further formulated "on demand" and as per application or route of administration with any type of aqueous solution (buffer, water for injection, saline, isotonic mixtures and others).

Thus, in some embodiments, the microemulsion is essentially devoid of water. The expression essentially devoid of water means to denote formulations that contain up to 10 wt % of water. In other embodiments, the formulation is free of water.

Cannabinoids are a group of psychoactive and non-psychoactive compounds which have an activity on cannabinoid receptors in cells to repress neurotransmitter release in the brain. The term is meant to encompass cannabinoids which are obtained from natural sources by various processes of treatment or extraction, as well as to synthetically obtained cannabinoids. The cannabinoid may be selected from one or more of cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CDB), cannabidiol monomethylether (CBDM), cannabidiol-$C_4$ (CBD-$C_4$), cannabidivarinic acid (CBDVA), cannabidiorcol (CBD-$C_1$), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid-$C_4$ (THCA-$C_4$), delta-9-tetrahydrocannabinol-$C_4$ (THCA-$C_4$), delta-9-tetrahydrocannabivarinic acid (THCVA), delta-9-tetrahydrocannabivarin (THCV), delta-9-tetrahydrocannabiorcolic acid (THCA-$C_1$), delta-9-tetrahydrocannabiorcol (THC-$C_1$), delta-7-cis-iso-tetrahydrocannabivarin, delta-8-tetrahydrocannabinolic acid A ($\Delta^8$-THCA), delta-8-tetrahydrocannabinol ($\Delta^8$-THC), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-$C_4$ (CBN-$C_4$), cannabivarin (CBV), cannabinol-$C_2$ (CBN-$C_2$), cannabiorcol (CBN-$C_1$), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahtdro-7-hydroxy-α-α-2-trimethyl-9-n-propyl-2,6-methano-2H-1-benzo xocin-5-methanol (OH-iso-HHCV), cannabiripsol (CBR), trihydroxy-delta-9-tetrahydroxycannabinol (triOH-THC), and any other cannabinoid.

In some embodiment, the cannabinoid is CBD or CBDA.

In other embodiments, the cannabinoid is THC.

In some embodiments, the cannabinoid-loaded formulation comprises between about 0.1 and 12 wt % of cannabinoid. In other embodiments, the cannabinoid-loaded formulation may comprise between about 0.1 and 11 wt % of cannabinoid, between about 0.1 and 10 wt % of cannabinoid, between 0.1 and 9 wt % cannabinoid, or between about 0.1 and 8 wt % of cannabinoid. In some other embodiments, the cannabinoid-loaded formulation may comprise between about 0.5 and 12 wt % of cannabinoid, between about 1 and 12 wt % of cannabinoid, between 1.5 and 12 wt % cannabinoid, or between about 2 and 12 wt % of cannabinoid. In additional embodiments, the cannabinoid-loaded formulation may comprise between about 0.5 and 11 wt % of cannabinoid, between about 1 and 10 wt % of cannabinoid, between 1.5 and 9 wt % cannabinoid, or between about 2 and 8 wt % of cannabinoid.

As noted above, the formulations of this disclosure comprises at least one oil, at least one hydrophilic surfactant, at least one co-surfactant, and at least 0.1 wt % of at least one cannabinoid, optionally further comprising at least one co-solvent.

The formulations of this disclosure may be further tailored to solubilize other components that may be present in the cannabinoid source, such as terpenes, essential oils, etc.

In the context of the present disclosure, the term oil refers to natural or synthetic oil in which the cannabinoid is dissolved. The oils used in the microemulsions of this disclosure should be approved for administration to a subject, including mineral oil, paraffinic oils, vegetable oils, glycerides, esters of fatty acids, liquid hydrocarbons and others.

According to some embodiments, the oil may be selected from medium-chain triglycerides (MCT), olive oil, soybean oil, canola oil, cotton oil, palmolein, sunflower oil, corn oil, rapeseed oil, grape seeds oil, hemp oil, pomegranate oil, avocado oil, peppermint oil, tomato oil, isopropyl myristate, oleyl lactate, coco caprylocaprate, hexyl laurate, oleyl amine, oleic acid, oleyl alcohol, linoleic acid, linoleyl alcohol, ethyl oleate, hexane, heptanes, nonane, decane, dodecane, D-limonene, neem oil, lavender oil, peppermint oil, anise oil, rosemary oil, sage oil, hibiscus oil, berries oil (any type), menthol, capsaicin, grape seed oil, pumpkin oil, hemp oil and similar essential oils or triglycerides or esters of fatty acids and mixtures thereof.

The oil may be present in the formulation, according to some embodiments, at an amount of between about 0.5 and 20 wt %. According to other embodiments, the oil is present in the formulation at an amount of between about 1 and 10 wt %.

The formulation comprise at least one hydrophilic surfactant. The term hydrophilic surfactant refers to ionic or non-ionic surfactants having a hydrophilic nature, i.e. a surfactant having an affinity for water. Exemplary surfactants are polyoxyethylene sorbitan monolaurate, polyoxyethylene sorbitan monopalmitate, polyoxyethylene sorbitan monooleate, and polyoxyeyhylene esters of saturated and unsaturated castor oil, ethoxylated monglycerol esters, ethoxylated fatty acids and ethoxylated fatty acids of short and medium and long chain fatty acids and others.

In some embodiments, the at least one hydrophilic surfactant is selected from polyoxyethylenes, ethoxylated (20EO) sorbitan mono laurate (T20), ethoxylated (20EO) sorbitan monostearate/palmitate (T60), ethoxylated (20EO) sorbitan mono oleate/linoleate (T80), ethoxylated (20EO) sorbitan trioleate (T85), castor oil ethoxylated (20EO to 40EO); hydrogenated castor oil ethoxylated (20 to 40EO), ethoxylated (5-40 EO) monoglyceride stearate/palmitate, polyoxyl 35 castor oil. According to other embodiments, the hydrophilic surfactant may be selected from Solutol HS15 (Polyethylene glycol (15)-hydroxystearate), polyoxyl 35 castor oil, polysorbate 40 (Tween 40), polysorbate 60 (Tween 60), polysorbate 80 (Tween 80), Mirj S40, oleoyl macrogolglycerides, polyglyceryl-3 dioleate, ethoxylated hydroxystearate, polyglycerol esters such as decaglycerol monolaurate, decaglycerol monooleate, hexaglycerol monooleate and hexaglycerol monolaurate, sucrose monooleate, sucrose monolaurate and similar.

The formulation may comprise, by some embodiments, between about 30 and 85 wt % of said hydrophilic surfactant. By some other embodiments, the formulation may comprise between about 35 and 80 wt % of hydrophilic surfactants.

The term co-surfactant should be understood to encompass any agent, different from the hydrophilic surfactant, which is capable (together with the hydrophilic surfactant) of lowering the interfacial tension between the oil phase and an aqueous phase to almost zero (or zero) allowing for the formation of a homogeneous mixture once the formulation is mixed with an aqueous liquid. According to some embodiments, the co-surfactant is selected from polyols, diglycerides, polyoxyethylenes, and others.

The co-surfactant may be at least one polyol, i.e. an alcohol containing at least 2 hydroxyl groups, for example ethylene glycol, glycerol, polyethylene glycol, polypropylene glycol, sorbitol, mannitol, lactitol, xylitol and others.

In some embodiments, the co-surfactant may be selected from glycerol, polypropylene glycol, polyethylene glycol, ethoxy hydrogenated castor oil, sorbitan esters of saturated or unsaturated fatty acids (Spans), phospholipids, waxes (carnauba, beeswax, candellila). In some embodiments, the co-surfactant is present in the formulation at an amount of between about 1 and 50 wt %. In other embodiments, the co-surfactant may be present in the formulation in an amount of between about 5 and 45 wt %.

The co-solvent may be a polyol, such as propylene glycol, glycerol, xylitol or short chain alcohols such as ethanol, propanol, iso-propanol and others.

The formulations described herein are spontaneously formed microemulsions, which are characterized by an energetic balance providing for a substantially zero interfacial tension. Such a balance is obtainable by the combination of surfactants and co-surfactants. Thus, in some embodiments, the ratio between the hydrophilic surfactants and the co-surfactants are between about 1:1 and 6:1 (wt/wt). In other embodiments, the ratio between the hydrophilic surfactants and the co-surfactants may be between about 1:1 and 4:1 (wt/wt).

The formulation may further comprise additional components. In some embodiments, the formulation further comprises at least one solvent. The term solvent refers to an organic compound, different from the oil, which is miscible in the oil and together therewith form a homogenous oily phase that dissolves and stabilizes the cannabinoid. The solvent may, according to some embodiments, be selected liquid hydrocarbons, alcohols, and others. According to some embodiments, the solvent may be selected from ethanol, propanol, isopropyl alcohol, acetic acid, propionic acid, fumaric acid, tartaric acid and it derivatives, lactic acid, maleic acid, malic acid, and others.

In some embodiments, the solvent may be present in the formulation at an amount of between about 0.1 and 25 wt %. In some other embodiments, the formulation may comprise between about 0.1 and 15 wt % of solvent.

Another additional component in the formulation may be, by some embodiments, at least one phospholipid. Phospholipids such as soy lecithin, rapeseed lecithin, corn or sunflower lecithins, egg lecithin, Epicorn 200, Phosal 50 PG, dioleyl phospatidylcholine (DOPC), oleyl palmytoyl phosphatidylcholine (POPC), and the corresponding serines, ethanol amines, glycerol, and others, may be used. According to such embodiments, the formulation may comprise between about 1 and 10 wt % of phospholipids.

In additional embodiments, the formulation described herein may additionally comprise at least one additive, selected from antioxidants (tocopherols), preservatives, membrane-piercing agents, transmembrane penetrating enhancers (such as transcutol, isosorbide, oleic acid, propylene glycol, maltodextrines, cyclodextrines, etc.), oil/water soluble vitamins, BHA, BHT, TBHQ, Propylate and its derivatives, and others.

In some embodiments, the formulation comprises (i) at least one cannabinoid, (ii) at least one oil selected from medium chain triglyceride (MCT), glycerin, glycerol, castor oil, R(+)-limonene, isopropyl myristate, ethyl laurate, ethyl caprate, olive oil, oleic acid, and triacetin, (iii) at least one hydrophilic surfactant selected from polysorbate 80 (Tween 80), polyoxyl 35 castor oil (cremophor castor oil), Mirj S40, HECO40 (ethoxy 40 hydrogenated castor oil), Labrasol (oleoyl macrogolglycerides), glycerol, and sucrose mono/dilaurate (iv) at least one co-surfactant selected from polypropylene glycol (PG), and Plurol Oleique CC 497 (Polyglyceryl-3 dioleate), and optionally at least one phospholipid and/or at least one solvent selected from oleic acid, transcutol, acetic acid, ethanol and isopropyl alcohol.

In other embodiments, the formulation is selected from the following formulations:

- at least one cannabinoid (e.g. CDB), medium chain triglyceride (MCT), polysorbate 80 (Tween 80), polyoxyl 35 castor oil (cremophor castor oil), polypropylene glycol (PG), ethanol, and at least one phospholipid; or
- at least one cannabinoid (e.g. CDB), medium chain triglyceride (MCT), glycerin, polysorbate 80 (Tween 80), polyoxyl 35 castor oil (cremophor castor oil), polypropylene glycol (PG), ethanol, and at least one phospholipid; or
- at least one cannabinoid (e.g. CDB), medium chain triglyceride (MCT), oleic acid, polysorbate 80 (Tween 80), polyoxyl 35 castor oil (cremophor castor oil), polypropylene glycol (PG), ethanol, and at least one phospholipid; or
- at least one cannabinoid (e.g. CDB), R-(+)-limonene, polysorbate 80 (Tween 80), polypropylene glycol (PG), and ethanol; or
- at least one cannabinoid (e.g. CDB), R-(+)-limonene, polysorbate 80 (Tween 80), polyoxyl 35 castor oil (cremophor castor oil), and polypropylene glycol (PG); or
- at least one cannabinoid (e.g. CDB), medium chain triglyceride (MCT), polysorbate 80 (Tween 80), polyoxyl 35 castor oil (cremophor castor oil), and polypropylene glycol (PG); or
- at least one cannabinoid (e.g. CDB), isopropyl myristate, polysorbate 80 (Tween 80), polyoxyl 35 castor oil (cremophor castor oil), and polypropylene glycol (PG); or
- at least one cannabinoid (e.g. CDB), ethyl laurate, polysorbate 80 (Tween 80), polyoxyl 35 castor oil (cremophor castor oil), and polypropylene glycol (PG); or
- at least one cannabinoid (e.g. CDB), MCT, glycerol, polysorbate 80 (Tween 80), polyoxyl 35 castor oil (cremophor castor oil), polypropylene glycol (PG), and ethanol; or
- at least one cannabinoid (e.g. CDB), MCT, glycerol, polysorbate 80 (Tween 80), polyoxyl 35 castor oil (cremophor castor oil), polypropylene glycol (PG), ethanol, and at least one phospholipid; or
- at least one cannabinoid (e.g. CDB), MCT, glycerol, polysorbate 80 (Tween 80), polyoxyl 35 castor oil (cremophor castor oil), polypropylene glycol (PG), ethanol, transcutol, and at least one phospholipid; or
- at least one cannabinoid (e.g. CDB), MCT, glycerol, polysorbate 80 (Tween 80), polyoxyl 35 castor oil (cremophor castor oil), polypropylene glycol (PG), ethanol, oleic acid, and at least one phospholipid; or
- at least one cannabinoid (e.g. CDB), MCT, glycerol, polysorbate 80 (Tween 80), polyoxyl 35 castor oil (cremophor castor oil), polypropylene glycol (PG), ethanol, transcutol, oleic acid, and at least one phospholipid; or
- at least one cannabinoid (e.g. CDB), R(+)-limonene, polysorbate 80 (Tween 80), polypropylene glycol (PG), and ethanol; or
- at least one cannabinoid (e.g. CDB), castor oil, polysorbate 80 (Tween 80), Mirj S40, polypropylene glycol (PG), ethanol, and at least one phospholipid; or
- at least one cannabinoid (e.g. CDB), MCT, polysorbate 80 (Tween 80), polyoxyl 35 castor oil (cremophor castor oil), polypropylene glycol (PG), ethanol, oleic acid, and at least one phospholipid; or
- at least one cannabinoid (e.g. CDB), ethyl caprate, polysorbate 80 (Tween 80), polypropylene glycol (PG), ethanol, and at least one phospholipid; or
- at least one cannabinoid (e.g. CDB), ethyl caprate, HECO 40, polyglyceryl-3 dioleate (CC497), polypropylene glycol (PG), acetic acid, and at least one phospholipid; or
- at least one cannabinoid (e.g. CDB), olive oil, Labrasol (oleoyl macrogolglycerides), polyglyceryl-3 dioleate (CC497), and ethanol; or
- at least one cannabinoid (e.g. CDB), olive oil, polysorbate 80 (Tween 80), polypropylene glycol (PG), ethanol, and at least one phospholipid; or
- at least one cannabinoid (e.g. CDB), MCT, polysorbate 80 (Tween 80), polyoxyl 35 castor oil (cremophor castor oil), polypropylene glycol (PG), and at least one phospholipid; or
- at least one cannabinoid (e.g. CDB), MCT, oleic acid, polysorbate 80 (Tween 80), polyoxyl 35 castor oil (cremophor castor oil), glycerol, polypropylene glycol (PG), ethanol, and at least one phospholipid; or
- at least one cannabinoid (e.g. CDB), Limonene, polysorbate 80 (Tween 80), polypropylene glycol (PG), and ethanol; or
- at least one cannabinoid (e.g. CDB), triacetin, polysorbate 80 (Tween 80), polypropylene glycol (PG), and at least one phospholipid; or
- at least one cannabinoid (e.g. CDB), triacetin, Labrasol (oleoyl macrogolglycerides), polyoxyl 35 castor oil (cremophor castor oil), polypropylene glycol (PG), isopropanol, and at least one phospholipid; or
- at least one cannabinoid (e.g. CDB), MCT, sucrose mono/dilaurate, polypropylene glycol (PG), isopropanol, and at least one phospholipid.

As will be demonstrated herein, the cannabinoid-loaded formulation stabilize the cannabinoid in acidic environments, and specifically in gastric fluid. When the cannabinoid is CBD, and the formulation may reduce the rate of transformation of the CBD into THC.

As explained above, the formulations of this disclosure are structured of nanometer size, substantially uniform, oil-solvated clusters or short domains of surfactants distributed in a water-free continuous phase. In some embodiments, the formulation may have an oil droplet size of between about 5 and about 100 nanometers, preferably between 10 to 30 nm.

The droplet size refers to the arithmetic mean of measured droplets' diameters, wherein the diameters range ±15% from the mean value.

In one of its aspects, this disclosure provides a process for preparing the cannabinoid-loaded formulation described herein, the process comprising mixing the microemulsion with a cannabinoid source.

Mixing may be carried out by any suitable known method that does not involve sheer-mixing, for example, manual mixing, magnetically stirring, mixing by pedals and others. In some embodiments, the mixing is carried out for between about 2-60 minutes. In other embodiments, the mixing is carried out at a temperature of between about 15-60° C.

The cannabinoid source is meant to refer to any source, natural, semi-synthetic or synthetic that contains the desired cannabinoid. In some embodiments, the cannabinoid source is selected from substantially pure cannabinoid (for example pure CBD), a cannabinoid in crystalline form, a natural cannabinoid source (for example a cannabis plant part), and a cannabinoid extract (obtained by any known extraction method).

When the source is a cannabinoid extract, such an extract may be obtained by oil extraction, solvent extraction and/or an extract obtained by $CO_2$ extraction.

In cases where the cannabinoid source is a natural cannabinoid source, it may, by some embodiments, be a plant from the genus *Cannabis*. The plant may be selected from *Cannabis sativa, Cannabis indica, Cannabis ruderalis*, and any mixture thereof. The plant may be any naturally-occurring strain, any horticultural variant, cultivated or engineered strain categorized in the *Cannabis* genus.

The process of this disclosure may be carried out utilizing any part of the plant source that may contain the cannabinoid; i.e. in some embodiments, the plant source is selected from *Cannabis* flowers, inflorescences, buds, fruit, pericarp, seeds, leaves, stems, stalks, roots, and any mixture thereof.

The plant source may be provided in any desired form, for example, as a, chopped, granulated, powder, granules, pellets, tablets, flakes, shreddings, or a plant part (e.g. intact leaves, seeds, intact inflorescence, etc.). The plant source may be provided fresh, frozen, freeze dried, semi-desiccated or desiccated.

When utilizing a plant as the source of the cannabinoid, the cannabinoid may be extracted from a plant source by utilizing the formulation of this disclosure. The term extraction or any lingual variation thereof, is meant to denote the transfer of a desired cannabinoid from the plant source to a solubilizing oily phase of the formulation. In such embodiments, the weight ratio (wt/wt) of the plant source to the formulation may be between 1:5 and 1:100.

Extraction is typically carried out by stirring or thoroughly mixing the formulation and the cannabinoid source, for example at 50-6000 rpm.

In other embodiments, the cannabinoid source is not a natural source in its native form (i.e. nor a plant part)\; namely, the source may be substantially pure cannabinoid (for example pure CBD), a cannabinoid in crystalline form, or a cannabinoid extract (obtained by any known extraction method).

At times, when seeking to increase the solubilization of the cannabinoid in the formulation, the formulation may be homogenized once the cannabinoid source and the other components of the formulation are mixed. Homogenization, or any lingual variation thereof, refers to the process of applying sheer forces onto mixtures to form intimate contact that permits the solubilization of the desired cannabinoid from the source. Homogenization may be carried out by any suitable means, including, but not limited to homogenizers and high speed mechanical stirring. It is of note that as the formulations used in the process of this disclosure have a nanometric size structure, the homogenization has little impact with respect to the micelles size and/or structure.

In some embodiments, the homogenization may be carried out for a period of time of between about 1 minute and about 60 minutes. In other embodiments, the homogenization is carried out for a period of between about 1 minute to 45 minutes, between about 1 minute and 30 minutes, or even between about 1 minute and 20 minutes. In some other embodiments, the homogenization may be carried our between about 5 minutes and about 60 minutes, between about 10 minutes and about 60 minutes, between about 15 minutes and about 60 minutes, or even between about 20 minutes and about 60 minutes.

In some embodiments, the homogenization may be carried out at a temperature of between about 5 and about 70° C. In other embodiments, the homogenization may be carried out at a temperature of between about 15 and about 70° C., between about 20 and about 70° C., between about 25 and about 70° C., or between about 30 and about 70° C. In some other embodiments, the homogenization may be carried out at a temperature of between about 10 and about 65° C., between about 10 and about 60° C., between about 10 and about 55° C., between about 10 and about 50° C., between about 10 and about 45° C., or even between about 10 and about 40° C. In further embodiments, the homogenization may be carried out at a temperature of between about 15 and about 60° C., between about 20 and about 50° C., or between about 25 and about 45° C.

Additional loading of the cannabinoid from the cannabinoid source may be carried out by employing additional cycles of solubilization, thereby maximizing the yield obtained from a given quantity of cannabinoid source.

The formulations of this disclosure may be used as is, namely as a substantially water-free concentrated form of cannabinoid, or may be diluted or further formulated into various pharmaceutical compositions. Thus, by another aspect, this disclosure provides a pharmaceutical or nutraceutical composition comprising the cannabinoid-loaded formulation as described herein.

The concentrate, as well as the diluted form of this disclosure, greatly increases the stability of the formulation over time, reduces the risk of contamination, broadens the scope of its application to a great variety of concentrations (various dose) and diluted forms, while permitting the medical professionals the decision how, when and which formulation to prepare prior to use.

The term concentrate (or any lingual variation thereof) denotes a substantially water-free, oil-based structured oil/surfactants system, in which surfactant tails are solubilized by the cannabinoid and the surfactant/co-surfactant system facilitating full dilution by a diluent aqueous phase (are dilutable) at will to form diluted formulation for administration. In other words, the concentrates are designed for fast and complete dilution in a suitable diluent, typically water for injection or saline, forming the diluted formulation, as will now be described. Upon dilution with a suitable diluent, the concentrate of the invention spontaneously forms microemulsions, which are at first "ill-defined solvated domains (or clusters) of surfactant" mesophases that upon minor dilution (ca. 20-30 wt %) form water-in oil nanodroplets; and upon further dilution transform to bicontinuous mesophases and into oil-in-water (O/W) nanodroplets, in which the diluent forms the continuous phase, while the oil phase is in the form of discrete droplets of nanometric size (i.e. the diluted formulation). As noted above, the diluted formulation are formed from the concentrate spontaneously, namely without the need to apply any shear, cavitation or homogenization processes.

In addition to providing flexibility in formulating and better control of the cannabinoid administration dose, the concentrates produced by the process described herein are substantially free, i.e. devoid, of water. Once water is absent from the formulation (i.e. up to 10 wt % water), the concentrates lack the environment sustaining microorganisms growth (e.g. fungi or bacteria), permitting longer storage without (or with minimal) risk of contamination. Without wishing to be bound by theory, one of the reasons due to which almost no bacterial contamination is observed for such concentrates may be the absence of unbound water, thereby limiting microbial growth and substantially extending the shelf life of the cannabinoid-loaded formulations.

The ratio between the concentrate and the diluent depends on the desired final concentration of cannabinoid in the formulation. According to some embodiments, the diluted formulation comprises between about 75 and about 98 wt % of the diluent.

In some embodiments, the composition may be formulated for lyophilization, i.e. by adding at least one sugar to the formulation, e.g. dextrin, lactose, mannitol, maltodextrin, erythritol, sorbitol, or any other suitable lyophilization additive.

In some embodiments, the pharmaceutical composition may comprise at least one pharmaceutically acceptable carrier. The "pharmaceutically/nutraceutically acceptable carriers" described herein, for example, vehicles, adjuvants, excipients, or diluents, are well-known to those who are skilled in the art and are readily available. It is preferred that the pharmaceutically acceptable carrier be one which is chemically inert to the active compounds and one which has no detrimental side effects or toxicity under the conditions of use.

The choice of carrier will be determined in part by the active agent (i.e. cannabinoid), as well as by the particular method used to administer the composition. Accordingly, there is a wide variety of suitable compositions of the pharmaceutical composition of the present invention.

The aqueous diluent may be selected from water, water for injection, saline, dextrose solution, water/alcohol mixtures, aqueous solutions (such as sugar and sweetener solutions and water-alcohol mixtures), or a buffer having a pH between 3 and 9 or any other isotonic solution or flavored water.

The cannabinoid is stably contained (i.e. solubilized) within the oil droplets, and is controllably released into the proper administration target. Without wishing to be bound by theory, the cannabinoid-oil-surfactant system forms strong reversible molecular interactions, thus permitting solubilization of the cannabinoid within the oil droplets of the microemulsion.

The pharmaceutical composition may comprise a variety of additional components, depending on the administration route and/or desired properties of the formulation, such as aqueous and non-aqueous diluents, isotonic sterile injection solutions, anti-oxidants, buffers, bacteriostats, suspending agents, solubilizers, thickening agents, gelling agent, emollients, moisturizers, stabilizers, preservatives, buffers, coloring agents, a fragrance, aromatic agents, flavoring agents, flavor masking agents, absorbers, filters, electrolytes, proteins, chelating agents, and others.

In some embodiments, the pharmaceutical composition is in a form selected from a gel, a lotion, oil, soap, a spray, an emulsion, a cream, an ointment, capsules, soft-gel capsules, chewing gum, a patch, buccal-patch and variety of other food products and supplements, or a solution.

In other embodiments, the formulation may be adapted for delivery of the cannabinoid in various routes of administration, including topical, buccal, oral, rectal, vaginal, transdermal, subcutaneous, intravenous, intramuscular, transdermal, intranasal, by inhalation, occularly or parenterally into the circulatory system of a subject.

Compositions suitable for oral administration can consist of (a) liquid solutions, such as an effective amount of the compound, or composition comprising same, dissolved in diluents, such as water, saline, or juice (e.g. orange juice); (b) capsules, sachets, tablets, lozenges, and troches, each containing a predetermined amount of the active ingredient, as solids or granules; (c) powders; (d) suspensions in an appropriate liquid; and (e) concentrates or diluted microemulsions (f) spray (g) inhalation. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active formulation in an inert base, such as gelatin and glycerin, or sucrose and acacia, emulsions, gels, and the like containing, in addition to the active formulation, such carriers as are known in the art.

Another aspect of the disclosure provides a cannabinoid-loaded formulation or a pharmaceutical composition of this disclosure, for use in treating a condition selected from pain associated disorders (as an analgesic), inflammatory disorders and conditions (as anti-inflammatory), apatite suppression or stimulation (as anoretic or stimulant), symptoms of vomiting and nausea (as antiemetic), intestine and bowl disorders, disorders and conditions associated with anxiety (as anxiolytic), disorders and conditions associated with psychosis (as antipsychotic), disorders and conditions associated with seizures and/or convulsions (as antiepileptic or antispasmodic), sleep disorders and conditions (as anti-insomniac), disorders and conditions which require treatment by immunosuppression, disorders and conditions associated with elevated blood glucose levels (as antidiabetic), disorders and conditions associated with nerve system degradation (as neuroprotectant), inflammatory skin disorders and conditions (such as psoriasis), disorders and conditions associated with artery blockage (as anti-ischemic), disorders and conditions associated with bacterial infections, disorders and conditions associated with fungal infections, proliferative disorders and conditions, disorders and conditions associated with inhibited bone growth, post trauma disorders, and others.

A further aspect, provides a method of treating a subject suffering from a condition selected from pain associated disorders, inflammatory disorders and conditions, apatite suppression or stimulation, symptoms of vomiting and nausea, intestine and bowl disorders, disorders and conditions associated with anxiety, disorders and conditions associated with psychosis, disorders and conditions associated with seizures and/or convulsions, sleep disorders and conditions, disorders and conditions which require treatment by immunosuppression, disorders and conditions associated with elevated blood glucose levels, disorders and conditions associated with nerve system degradation, inflammatory skin disorders and conditions, disorders and conditions associated with artery blockage, disorders and conditions associated with bacterial infections, disorders and conditions associated with fungal infections, proliferative disorders and conditions, and disorders and conditions associated with inhibited bone growth, post trauma disorders and others, the method comprising administering to the subject an effective amount of the cannabinoid-loaded formulation or the pharmaceutical composition of this disclosure.

The formulations described herein may be used as such to induce at least one effect, e.g. therapeutic effect, or may be associated with at least one cannabinoid, which is capable of inducing, enhancing, arresting or diminishing at least one effect, by way of treatment or prevention of unwanted conditions or diseases in a subject. The at least one agent (substance, molecule, element, compound, entity, or a combination thereof) may be selected amongst therapeutic agents, i.e. agents capable of inducing or modulating a therapeutic effect when administered in a therapeutically effective amount, and non-therapeutic agents, i.e. which by themselves do not induce or modulate a therapeutic effect but which may endow the pharmaceutical composition with a selected desired characteristic.

The pharmaceutical compositions of the present disclosure may be selected to treat, prevent or ameliorate any pathology or condition. The term treatment or any lingual variation thereof, as used herein, refers to the administering of a therapeutic amount of the composition or system described herein, whether in a concentrate form or in a diluted formulation form, which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

As known, the effective amount for purposes herein may be determined by such considerations as known in the art. The effective amount is typically determined in appropriately designed clinical trials (dose range studies) and the person versed in the art will know how to properly conduct such trials in order to determine the effective amount. As generally known, the effective amount depends on a variety of factors including the distribution profile within the body, a variety of pharmacological parameters such as half-life in the body, on undesired side effects, if any, on factors such as age and gender, and others.

The term "subject" refers to a mammal, human or non-human.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between. It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

As used herein, the term "about" is meant to encompass deviation of ±10% from the specifically mentioned value of a parameter, such as temperature, pressure, concentration, etc.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Formulations and Preparations

Figure 1:
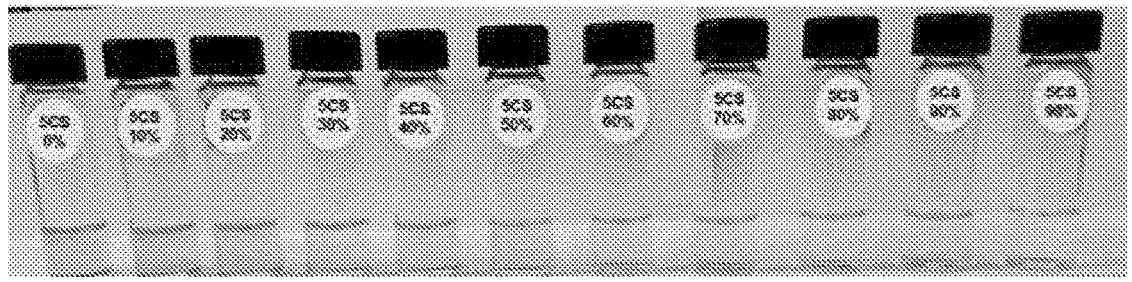
FIG. 1 shows CBD-loaded 5CS formulation in various dilutions.

Exemplary microemulsions described herein are provided in Tables 1-1 to 1-5. As noted above, the formulations are self-assembled systems which are formed in a spontaneous manner. Therefore, several compositions of the formulations were prepared by simple mixing of ingredients at 25-70° C. An exemplary process for preparing the formulation involves mixing together the oil, the surfactant and the co-surfactant (and where applicable also a solvent, a co-solvent and/or a phospholipid) until a homogenous, clear (transparent) mixture is obtained. In case the surfactants or oil are solid at room temperature, heating can be applied while mixing to allow full dissolution and formation of the empty formulation.

The formulation is then slowly added to a cannabinoid source, for example a plant part or pure cannabinoid, to allow appropriate wetting and then mixed and/or homogenized. Another variation of the process includes adding the cannabinoid source stepwise to the empty (un-loaded) formulation until a homogeneous slurry is obtained.

Solubilization was carried out under heating and/or inert atmosphere, thereby solubilizing the desired cannabinoid, in this case CBD, into the formulation.

TABLE 1-1

Formulations (all amounts provided in wt %)

| | | Formulation | | | | |
|---|---|---|---|---|---|---|
| | Component | 5CS | 5CS(1) | 5CS(2) | 5CS(3) | 5CS(6) |
| Oil | MCT | 3.60 | 3.60 | 3.60 | 3.60 | 3.63 |
| | Glycerin | — | 19.0 | 11.40 | — | — |
| Hydrophilic surfactant | Polysorbate 80 (Tween 80) | 35.37 | 28.37 | 30.0 | 35.37 | 35.64 |
| | Cremophor EL castor oil* | 42.57 | 35.57 | 40.0 | 42.57 | 42.9 |
| Co-surfactant | Propylene glycol (PG) | 12.66 | 7.66 | 9.2 | 12.18 | 12.28 |
| Solvent | Ethanol | 0.2 | 0.2 | 0.2 | 0.2 | 0.17 |
| | Oleic acid | — | — | — | 0.48 | — |
| Phospholipid | PC (Phosphatiydyl Choline) | 5.3 | 5.3 | 5.3 | 5.3 | 5.28 |
| | Lyso-PC (Lysophosphatydil choline) | 0.3 | 0.3 | 0.3 | 0.3 | — |
| | CBD loading | ≤5 | ≤2.5 | ≤5 | ≤5 | ≤5 |

*Polyoxyl 35 castor oil

TABLE 1-2

Formulations (all amounts provided in wt %)

| | | Formulation | | | | | | |
|---|---|---|---|---|---|---|---|---|
| | Component | AX1 | NL28B | NL28B(1) | NL28B(2) | NL28B(3) | NL28B(4) | NL28I |
| Oil | MCT | — | — | 6.55 | — | — | — | — |
| | Castor oil | — | 6.55 | — | — | — | — | 5.4 |
| | R(+)-Limonene | 5 | — | — | 6.55 | — | — | — |
| | Isopropyl myristate | — | — | — | — | 6.55 | — | — |
| | Ethyl laurate | — | — | — | — | — | 6.55 | — |
| Hydrophilic surfactant | Tween 80 | 45 | 36.34 | 36.34 | 36.34 | 36.34 | 36.34 | 23.60 |
| | Cremophor EL | — | 37.64 | 37.64 | 37.64 | 37.64 | 37.64 | 26.40 |
| Co-surfactant | PG | 45 | 19.47 | 19.47 | 19.47 | 19.47 | 19.47 | 44.60 |
| Solvent | Ethanol | 5 | — | — | — | — | — | — |
| | CBD loading | ≤10 | ≤5 | ≤5 | ≤5 | ≤5 | ≤5 | ≤5 |

TABLE 1-3

Formulations (all amounts provided in wt %)

| | | Formulation | | | | | | |
|---|---|---|---|---|---|---|---|---|
| | Component | In9 | In9(1) | In9(2) | In9(3) | In9(4) | In9(5) | In9(6) |
| Oil | MCT | 11.5 | 11.5 | 11.5 | 11.5 | 11.5 | 5.0 | 5.0 |
| | Glycerol | 6.5 | 6.5 | 6.5 | 6.5 | 6.5 | 6.5 | 6.5 |
| Hydrophilic surfactant | Tween 80 | 35.0 | 35.0 | 35.0 | 35.0 | 35.0 | 35.0 | 35.0 |
| | Cremopor EL | 35.0 | 34.0 | 30.0 | 30.0 | 30.0 | 32.0 | 32.0 |

TABLE 1-3-continued

Formulations (all amounts provided in wt %)

| Component | | In9 | In9(1) | In9(2) | In9(3) | In9(4) | In9(5) | In9(6) |
|---|---|---|---|---|---|---|---|---|
| Co-surfactant | PG | 6.5 | 6.5 | 6.5 | 6.5 | 4.0 | 6.5 | 6.5 |
| Solvent | Ethanol | 5.5 | 5.5 | 5.5 | 3.0 | 3.0 | 5.0 | 6.5 |
|  | Oleic acid | — | — | — | — | 5.0 | 2.5 | 2.5 |
|  | Transcutol | — | — | — | 2.5 | — | 2.5 | 2.5 |
| Phospholipid or surfactant | PC | — | 1.0 | 5.0 | 5.0 | 5.0 | 5.0 | 5.0 |
| CBD loading | | ≤5 | ≤5 | ≤5 | ≤5 | ≤5 | ≤5 | ≤5 |

TABLE 1-4

Formulations (all amounts provided in wt %)

| Component | | MM7(2) | 2BR(9:1) | 2CA(9:1) | 2BR(8:2) |
|---|---|---|---|---|---|
| Oil | R(+)-Limonene | — | 5.0 | 5.0 | 10.0 |
|  | Castor oil | 2.9 | — | — | — |
| Hydrophilic surfactant | Tween 80 | 45.0 | 45.0 | 60.0 | 53.3 |
|  | Mirj S40 | 32.9 | — | — | — |
| Co-surfactant | PG | 45.0 | 45.0 | 30.0 | 23.67 |
| Solvent | Ethanol | 5.0 | 5.0 | 5.0 | 10.0 |
| CBD loading | | ≤5 | ≤3 | ≤3 | ≤4 |

TABLE 1-5

Formulations (all amounts provided in wt %)

| Component | | 5CS(5) | 5CS(7) | 5CS(8) | CAS(1) | CAS(2) | CAS(3) | CAS(4) |
|---|---|---|---|---|---|---|---|---|
| Oil | MCT | 3.63 | 3.63 | 3.63 | — | — | — | — |
|  | Ethyl caprate | — | — | — | 7.5 | 7.5 | — | — |
|  | Olive oil | — | — | — | — | — | 4.2 | 5.0 |
| Hydrophilic surfactant | Tween 80 | 35.64 | 35.64 | 33.03 | 15 | — | — | 17.14 |
|  | Cremophor EL | 42.90 | 40.32 | 42.57 | — | — | — | — |
|  | Heco40* | — | — | — | — | 15 | — | — |
|  | Labrasol** | — | — | — | — | — | 61 | — |
| Co-surfactant | PG | 12.38 | 10.22 | 6.3 | 50 | 25 | — | 57.14 |
|  | CC497*** | — | — | — | — | 25 | 21 | — |
| Solvent | Ethanol | 0.17 | 0.17 | 0.17 | 22.5 | — | 12.8 | 15.0 |
|  | Oleic acid | — | 4.5 | 4.5 | — | — | — | — |
|  | Acetic acid | — | — | — | — | 22.5 | — | — |
| Phospholipid | PC | 5.24 | 5.24 | 5.24 | 5 | 5 | — | 5.71 |
|  | Lyso-PC | — | 0.08 | 0.08 | — | — | — | — |
| CBD loading | | ≤5 | ≤5 | ≤5 | ≤5 | ≤5 | ≤5 | ≤5 |

*ethoxy 40 hydrogenated castor oil
**Labrafil M1944CS (Oleoyl macrogolglycerides)
***Plurol Oleique CC 497 (Polyglyceryl-3 dioleate)

Characterization of CBD-Loaded Formulations

Empty and CBD-loaded (1 wt %) 5CS systems were characterized using several methods in order to elucidate structural changes as well as the effect of CBD on the formulation. Electrical conductivity, rheology measurements, differential scanning calorimetry, dynamic light scattering and others were utilized to identify phase transitions and changes at the molecular level within the systems.

Dilutability

As shown in FIG. 1, CBD-loaded 5CS system was diluted by mixing with up to 9% water. The system remains clear and is fully dilutable, without any phase separation.

Electrical Conductivity Measurements

Structural transitions of the system as a result of dilution was carried out by electrical conductivity measurements. In order to facilitate measurement, the 5CS systems were diluted with 0.01M solution of NaCl. Measurements carried out at RT (23±2° C., using conductivity meter 730 (Metler Toledo, GmBH, Switzerland) equipped with 180×65 mm/0.61 kg electrode (conductivity range of 0.01 µS/cm-1000 mS/cm). The results are depicted in FIG. 2.

Figure 2:
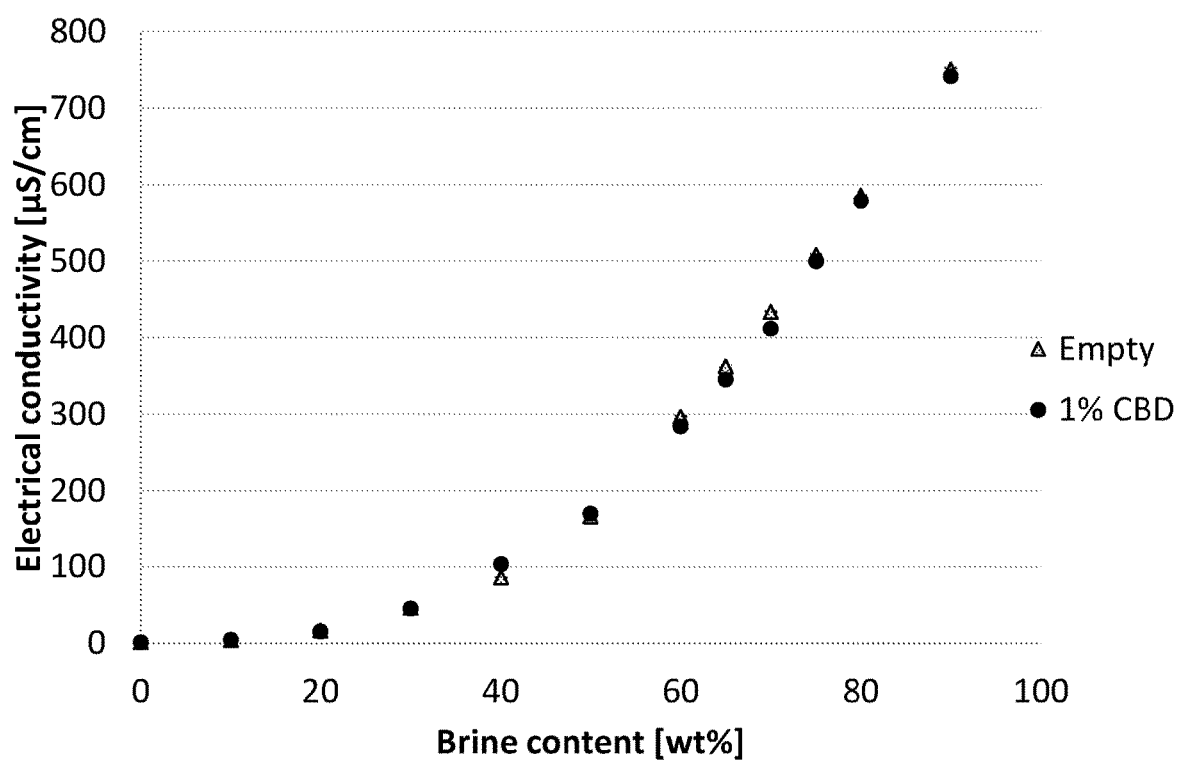
FIG. 2 shows electrical conductivity of empty and CBD-loaded 5CS formulation as a function of water (0.01M NaCl) content.

As can be seen in FIG. 2, which present the electrical conductivity of the empty and CBD loaded systems versus water content, no significant effect is seen as a result of the solubilization of CBD; these results indicate that the formulation may be uniquely tailored to entrap the cannabinoid, in this case CBD, into the interface or to the oil core of the formulation. FIG. 2 also demonstrates that incorporation of CBD into the system has no effect on the stability, disruption or physical changes of the system throughout the whole dilution process (ratio).

Further, FIG. 2 confirms that at low water content (of ca. 20 wt % water) the system is of W/O nano-droplets and transforms into bicontinuous phase (sharp increase in the conductivity), and inverts into O/W droplet (sharp decrease in the conductivity) as a result of dilution effect.

Viscosity Measurements

Viscosity measurements as a function of the dilution were carried out at RT (25±0.1° C.), using Thermo Haake Rheo Scope 1 equipped with C60/° 1 cone and glass plate (the distance between the cone and the plate during the measurements was 0.022 mm). At each measurement increasing shear rates (0-100 $s^{-1}$) were applied for 6 min.

Figure 3:
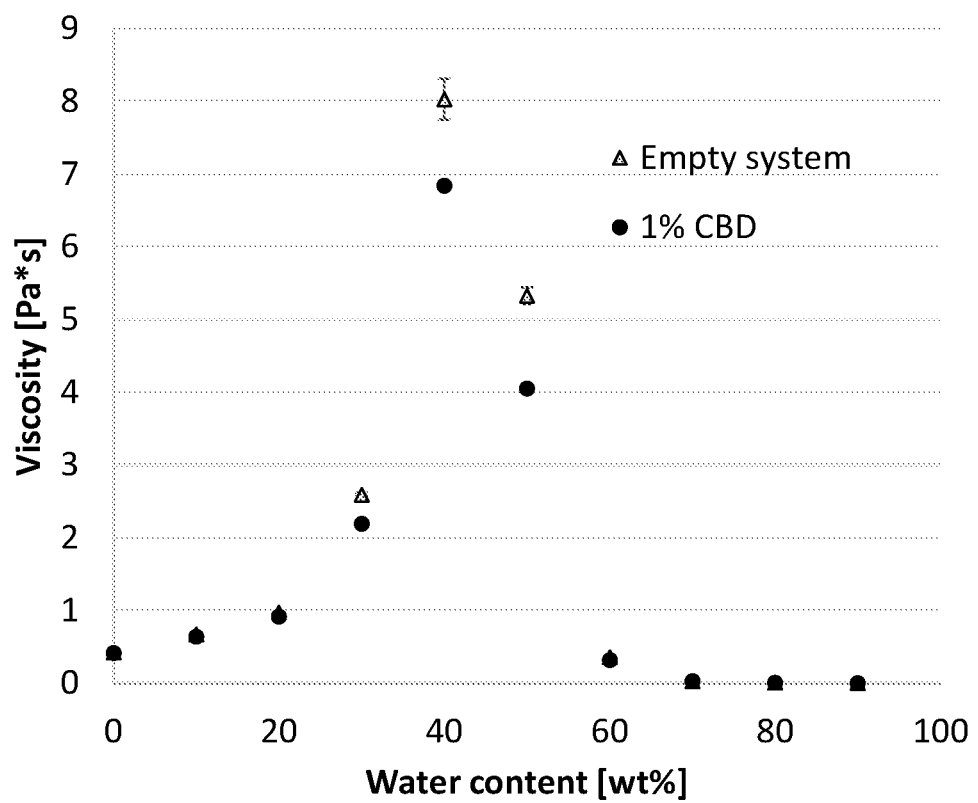
FIG. 3 shows viscosity of empty and CBD-loaded 5CS formulation as a function of the water content.

As seen in FIG. 3, when W/O nano-droplets are formed (ca. up to 20 wt % water) the CBD is located in the outer interface close to the oil and does not interfere with the entanglement of the surfactant tails; similarly, when the system inverts into O/W nano-droplets, the CBD has no effect on the entanglement of the surfactant since it located mostly in the oil core.

However, significant differences in viscosity are identified between 30 to 50 wt % water between the CBD-loaded system and the empty system. Without wishing to be bound by theory, the CBD molecules interfere with the entanglements between the surfactant's lipophilic tails only at the bicontinuous region where the system is mostly composed of interfaces weakening these interactions, thereby resulting in lower viscosity values compared to the empty (non-loaded) formulation.

Differential Scanning Calorimetry (DSC)

The melting/freezing temperature of the water changes as a function of the water molecules environment. Therefore, changes in such temperature may be used to characterize the interaction of water molecules with other species in the system. In order to follow these changes, sub-zero calorimetric measurements were carried out. 8-12 mg samples of 5CS system with different water dilutions, unloaded and 1 wt % CBD-loaded, were cooled from 25° C. to −100° C. and then heated back to 25° C. both at a rate of 5° C./min (using a Mettler Toledo DSC 822). Between cooling and heating the sample kept at an isotherm of −100° C. for 20 min. All measurements were carried out against empty perforated pan as a reference. Melting temperatures and enthalpy of transition for the different samples are presented in Table 3.

TABLE 3 melting temperatures and melting enthalpies of water within 5CS, empty and CBD-loaded systems

| Water content | Empty system | | 1% CBD-loaded system | |
|---|---|---|---|---|
| (wt %) | $T_m$ (° C.) | $\Delta H_m$ (J/g) | $T_m$ (° C.) | $\Delta H_m$ (J/g) |
| 30 | −26.0 | 1.39 | −27.3 | 1.25 |
| 40 | −17.9 | 28.05 | −18.9 | 33.05 |
| 50 | −8.5 | 46.1 | −12.6 | 47.95 |
| 60 | −4.8 | 65.80 | −6.3 | 96.15 |
| 70 | −3.8 | 127.21 | −4.3 | 136.89 |
| 80 | −2.1 | 162.56 | −2.8 | 186.96 |
| 90 | −0.8 | 206.96 | −1.8 | 241.99 |

Beyond 30 wt % water no endothermic peaks appeared, meaning that the water are tightly bound and are found predominantly in the core of the droplet. Above 30% water, the melting temperature and enthalpy increases as water is released from the droplets; in high water concentrations (i.e. high dilutions) most of the water is free. Yet from the values of the $\Delta H_m$ it is clear that even at 90 wt % water not all the water is free since the $\Delta H_m$ of free water is ca. −280 J/g.

The thermal behavior of the systems indicates that at low water contents the (0-40%) the water is bound to the surfactants and freezes at −30-(−20)° C. At higher water contents the water graduate becomes freer and freezes at higher temperatures closely to 0° C. (above 60 wt % water). That is to say that above 60 wt % of water the continuous phase is the water. At lower water contents (30-50) the water creates continuous domains together with oil continuous domains to create the so called bicontinuous mesophase. Beyond 30 wt % dilution the water is tightly bound to the polyethoxylated head group of the surfactants. The major differences between the empty and loaded system are reflecting the freedom of water to move (mobility)—once the CBD is entrapped into the core it is associated with the head group of the surfactant, and as a result more water molecules are free to be mobile.

Dynamic Light Scattering (DLS)

The oil droplet size of water-diluted formulations was determined by DLS measurements, as well as analysis of drop diffusion coefficient of oil in water. The results of the DLS measurements are provided in Table 4.

TABLE 4

Droplet size and droplet diffusion coefficient of 5CS, empty and 1 wt % CBD-loaded systems

| | Empty system | | 1% CBD-loaded system | |
|---|---|---|---|---|
| Water content (wt %) | Droplet diameter (nm) | Diffusion coef. (μm²/s) | Droplet diameter (nm) | Diffusion coef. (μm²/s) |
| 70 | 11.3 ± 0.2 | 40.2 | 11.6 ± 0.15 | 40.0 |
| 80 | 10.1 ± 0.2 | 48.7 | 10.3 ± 0.25 | 44.1 |
| 90 | 10.1 ± 0.2 | 48.7 | 10.3 ± 0.2 | 48.6 |

Typically, solubilization of guest molecules within the formulation causes the swelling of the droplets and increases their diameter. In the 5CS system, the results show that the effect of the solubilization is not significant. This may be due to the relatively low concentration of CBD within the microemulsion.

The diffusion coefficients of the systems at different dilutions are correlative with drops size—the larger the diameter the slower the drop diffusivity.

Self-Diffusion NMR (SD-NMR)

In order to determine the structure of the oil droplets (or micelles) of the formulations, self-diffusion NMR analysis was carried out. SD-NMR is able to locate each component within the NSSL via measurements of its diffusion coefficient. Rapid diffusion (>100×10$^{-11}$ m$^2$s$^{-1}$) is characteristic of small molecules, free in solution, while slow diffusion coefficients (<0.1×10$^{-11}$ m$^2$s$^{-1}$) suggest low mobility of macromolecules or bound/aggregated molecules.

NMR measurements were performed with a Bruker AVII 500 spectrometer equipped with GREAT 1/10 gradients, a 5 mm BBO and a 5 mm BBI probe, both with a z-gradient coil and with a maximum gradient strength of 0.509 and 0.544 T m$^{-1}$, respectively. Diffusion was measured using an asymmetric bipolar longitudinal eddy-current delay (bpLED) experiment, or and asymmetric bipolar stimulated echo (known as one-shot) experiment with convection compensation and an asymmetry factor of 20%, ramping the strongest gradient from 2% to 95% of maximum strength in 32 steps. The spectrum was processed with the Bruker TOP-SPIN software. NMR spectra were recorded at 25±0.2° C. The components were identified by their chemical shift in 1H NMR.

Figure 4A:
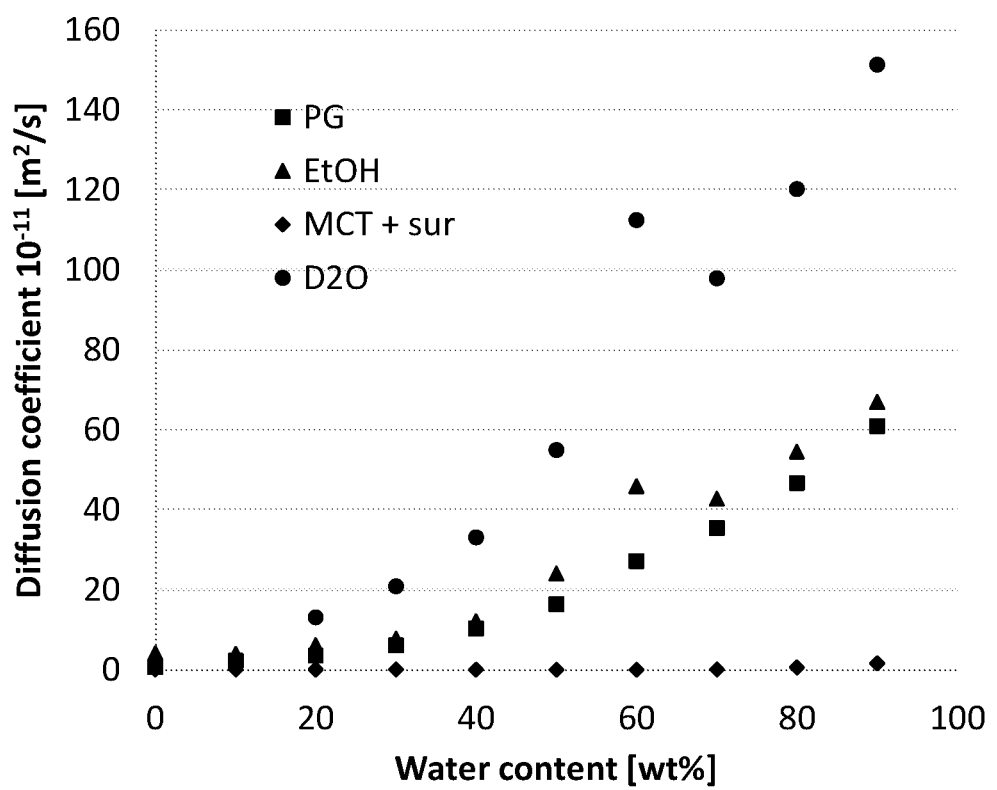
FIGS. 4A-4B show the diffusion coefficients (Dx) of the various components for unloaded and 1 wt % CBD-loaded formulation, respectively.
Figure 4B:
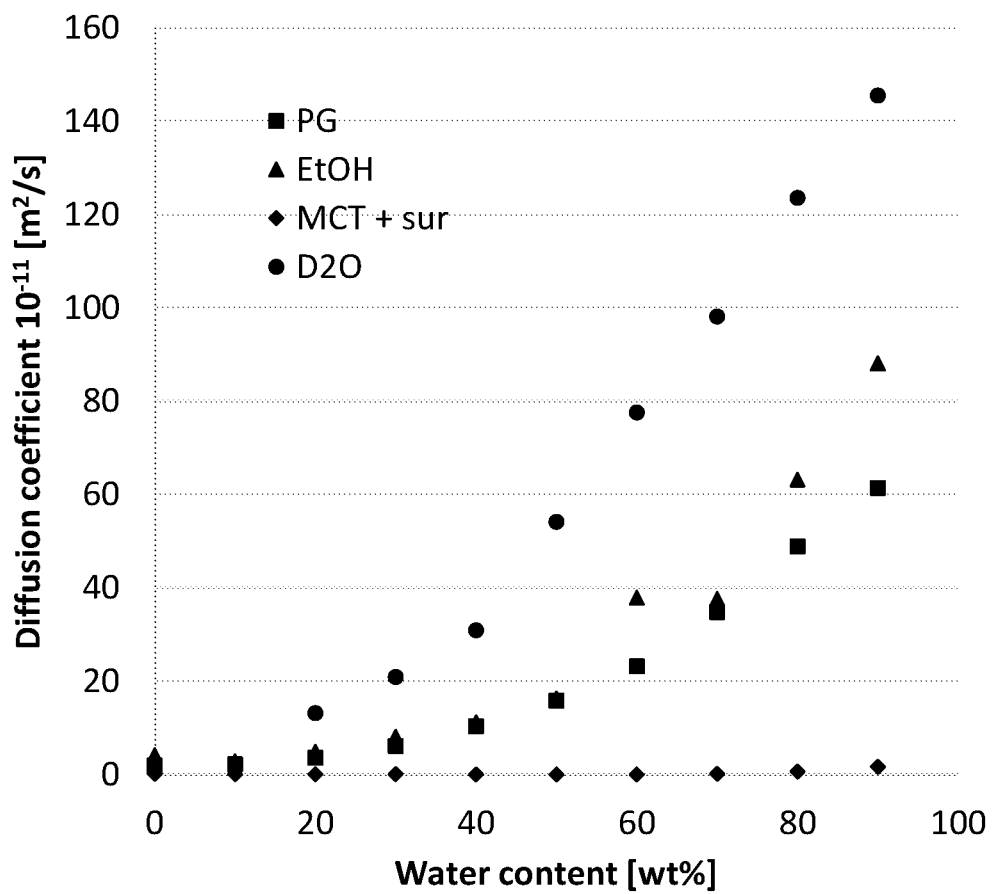

FIGS. 4A-4B show the diffusion coefficients (Dx) of the various components for unloaded and 1 wt % CBD-loaded formulations, respectively.

As noted above, the formulations of this disclosure are constituted by oil droplets which solubilize CBD surrounded by surfactants and co-surfactants. When in the concentrate form (i.e. in the absence of water), the system is arranged in a reverse micelle structure, and when mixed with small amounts of aqueous media, hydrated and solvated surfactants are formed. Upon further dilution with aqueous phase oil-in-water (O/W) nanodroplets entrapping into their oil core the CBD molecules are formed. When diffusion coefficients of CBD and the surfactant are of a similar order of magnitude (when measured in the microemulsion system), the CBD will remain entrapped within the oil core during the structural transformations of the system (i.e. the changes in structure due to dilution); this is a result of the interactions (physical complexation) between the CBD and the surfactants and/or co-surfactants, thus stabilizing the formulation and preventing undesired release of the CBD from the oil core. Release of the CBD from the formulation will occur upon interaction of the droplets with target biological membranes after administration to the subject to be treated.

FIGS. 3A and 3B indicate that the mobility of all the components are not significantly affected by the solubilization of the CBD in the nanodroplets. Although CBD's chemical shift could not be detected by this NMR technique, the fact that no change was measured in all other components indicated that CBD is completely solubilized throughout the entire dilution process. The mobility of the surfactant is very low, indicating that the CBD is interacting with the surfactant and is in the proximity of the surfactant at the interface.

Stability of Formulations with CBD from a Plant Source

5CS and In9(6) formulations (see Table 5-1) were loaded with 5 wt % CBD and incubated at three different temperature (4, 25 and 40° C.) under different conditions (without protection, with the addition of 600 ppm α-tocopherol acetate and under nitrogen atmosphere). Both the concentrate and a diluted microemulsion (80% water) were tested.

TABLE 5-1

Formulations for stability tests

| | Formulation 5CS | | Formulation In9(6) | |
|---|---|---|---|---|
| | Component | wt % | Component | wt % |
| Oil | MCT | 3.6 | MCT | 5 |
| | | | Oleic acid | 2 |
| Hydrophilic surfactant | Polysorbate 80 (Tween 80) | 35.37 | Polysorbate 80 (Tween 80) | 35 |
| | Cremophor EL castor oil* | 42.57 | Cremophor EL castor oil* | 32 |
| | | | Glycerol | 6.5 |
| Co-surfactant | Propylene glycol (PG) | 8.46 | Propylene glycol (PG) | 9 |
| Solvent | — | — | Ethanol | 5.5 |
| Phospholipid | Phosal 50 PG** | 10 | Phosphatidylcholine | 5 |

*Polyoxyl 35 castor oil
**Phosal 50 PG composed of 1.5-2.5% wt ethanol, >500 ppm ethylenemethylketone, 0.5 wt % water, 33.8-41.2 wt % propylene glycol, <50.0 wt % phosphatidylcholine, >6 wt % lyso-phosphatidylcholine The visual appearance of the samples were recorded after 30 days of incubation. The results are detailed in Table 5-2.

TABLE 5-2

Stability of CBD-loaded formulations

| | | 5CS | | In9(6) | |
|---|---|---|---|---|---|
| Extraction Conditions | Incubation temperature | Concentrate | 80% dilution | Concentrate | 80% dilution |
| No protection | 4° C. | Stable | Stable | Stable | Stable |
| | 25° C. | Stable | Stable | Stable | Stable |
| | 40° C. | Yellowish | N/A | Yellowish | N/A |
| 600 ppm α-tocopherol acetate | 4° C. | Stable | Stable | Stable | Stable |
| | 25° C. | Stable | Stable | Stable | Stable |
| | 40° C. | Yellowish | Stable | Yellowish | Stable |
| Nitrogen atmosphere | 4° C. | Stable | Stable | Stable | Stable |
| | 25° C. | Stable | Stable | Stable | Stable |
| | 40° C. | Stable | Stable, Yellow | Stable | Stable, Yellow |

As clearly seen, the CBD-loaded formulations are stable over a wide variety of conditions, namely most of the tested samples remained transparent, without any indication of phase separation or precipitation.

Stability of Pure CBD Solubilized in AX-1 and 5CS Formulations

Crystalline CBD was solubilized in a concentration of 5 wt % in AX-1 and 5CS formulations under various conditions: addition of 1000 ppm of vitamin E acetate, under passive diffusion of nitrogen or under no special treatment. All samples were kept at three different temperatures of 4° C., 25° C. and 40° C., four samples of each formulation/treatment for an examination at four time-points including 0 (initial), 15, 30 and 60 days. All samples (2 mL) were kept at 4 ml vials with coordinated labeled. Some of the samples were passively purged with nitrogen. At the predetermined times of sampling, the suitable samples were tested for their appearance and were analyzed by HPLC to determine CBD concentration and presence/absence of degradation products.

Figure 5A:
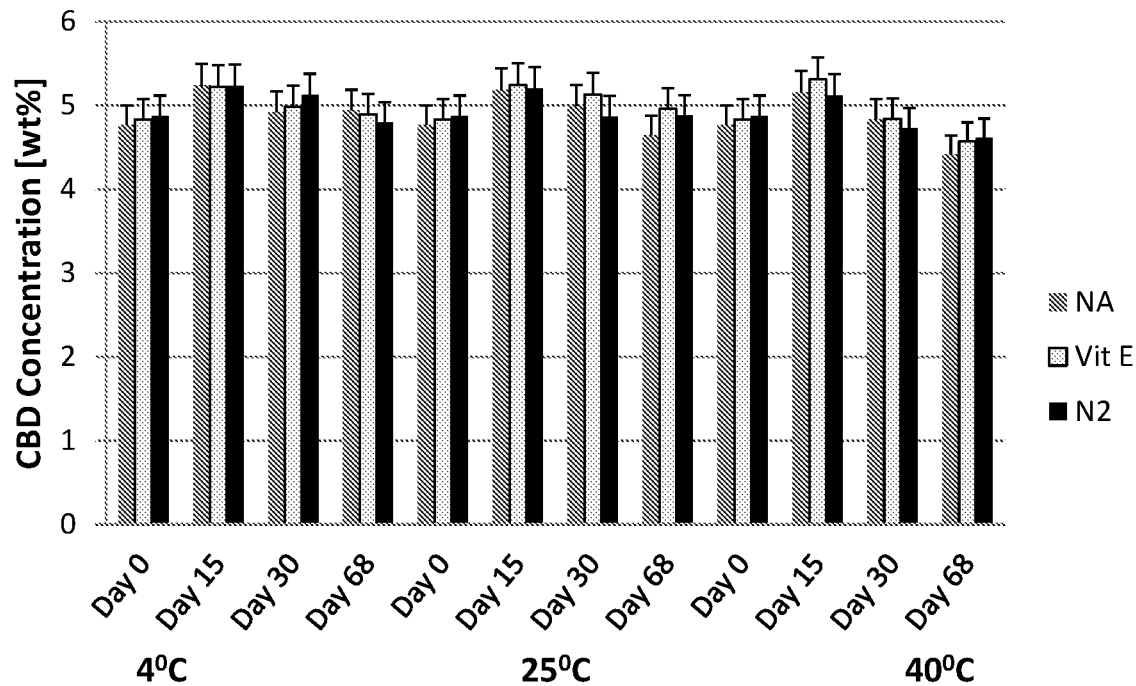
FIGS. 5A and 5B show long term stability of crystalline CBD solubilized in a concentration of 5 wt % in AX-1 and 5CS formulations, respectively.
Figure 5B:
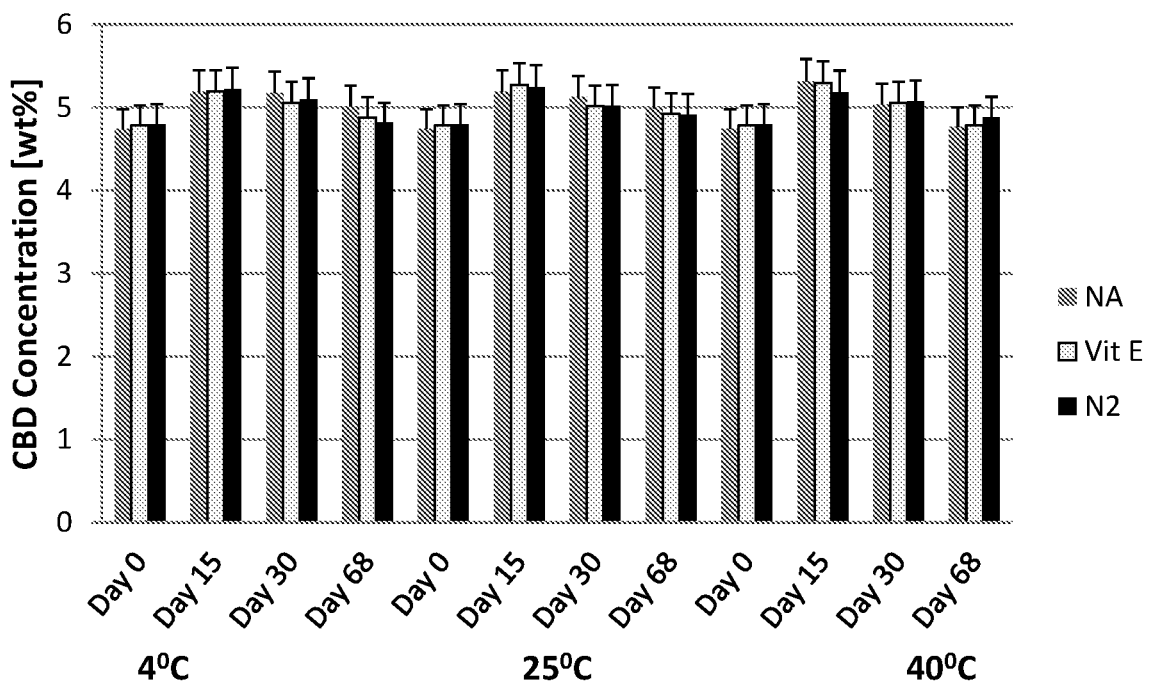

No significant changes in CBD concentration of AX1 and 5CS concentrates was detected after 60 days for all storage temperatures, as seen in FIGS. 5A and 5B, respectively.

Stability LumiFuge™ Tests

To determine long term stability of formulations, a rapid measurement was carried out using LUMiFuge™ analytical centrifugation. LUMiFuge analysis enables to predict the shelf-life of a formulation in its original concentration, even in cases of slow destabilization processes like sedimentation, flocculation, coalescence and fractionation. During LUMiFuge measurements, parallel light illuminates the entire sample cell in a centrifugal field; the transmitted light is detected by sensors arranged linearly along the total length of the sample-cell. Local alterations of particles or droplets are detected due to changes in light transmission over time. The results are presented in a graph plotting the percentage of transmitted light (Transmission %) as a function of local position (mm), revealing the corresponding transmission profile over time. CBD-loaded AX1 formulations in concentrate form and with 85% water dilution were tested in comparison to the commercial product "Plus CBD oil" by CS Science (formulations tested as is, without any further treatment).

Figure 6A:
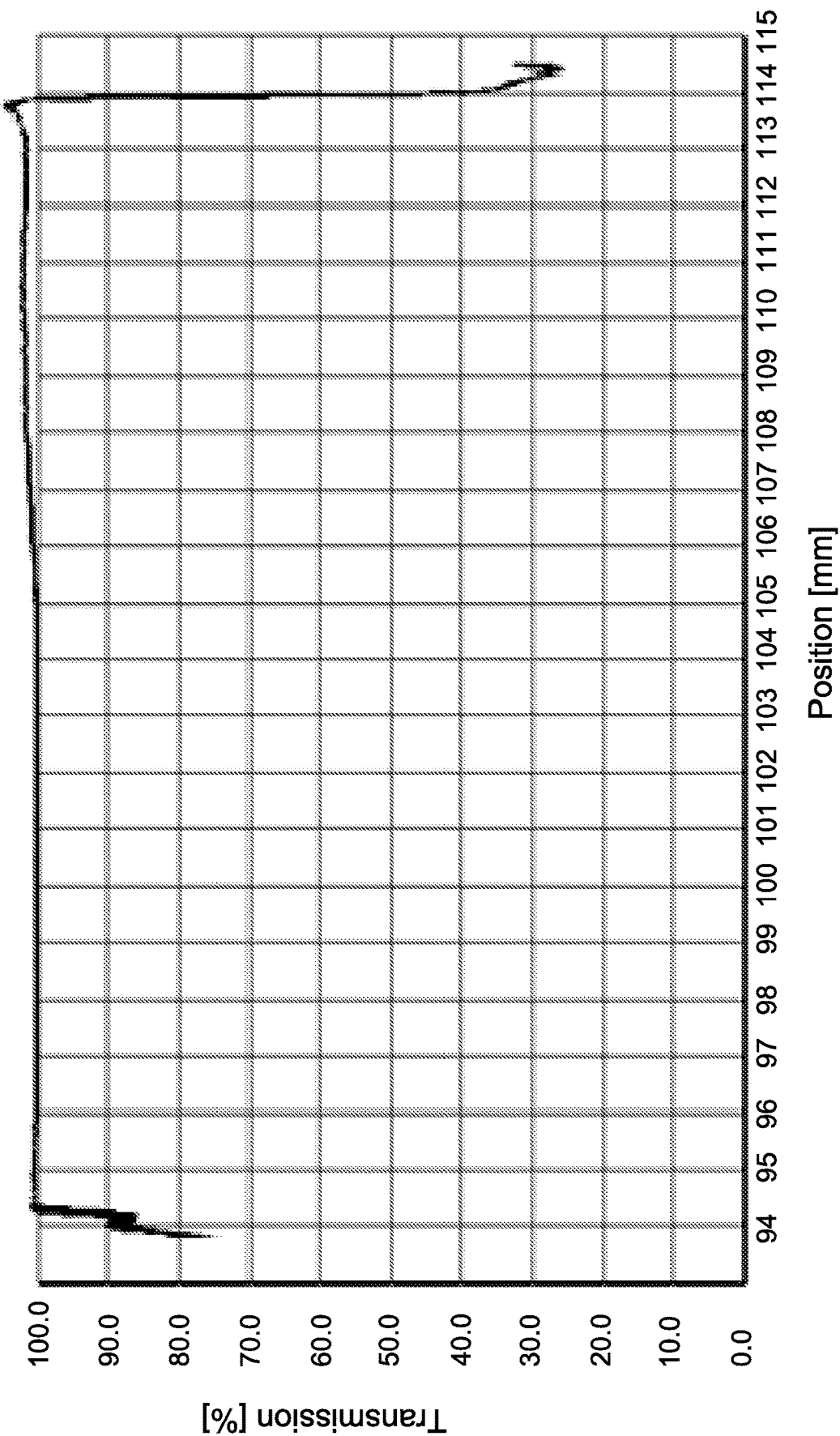
FIGS. 6A-6C show LUMiFuge™ test results for CBD-loaded AX-1 concentrate, CBD-loaded AX-1 85 wt % water diluted, and commercial 'Plus CBD' product, respectively.
Figure 6B:
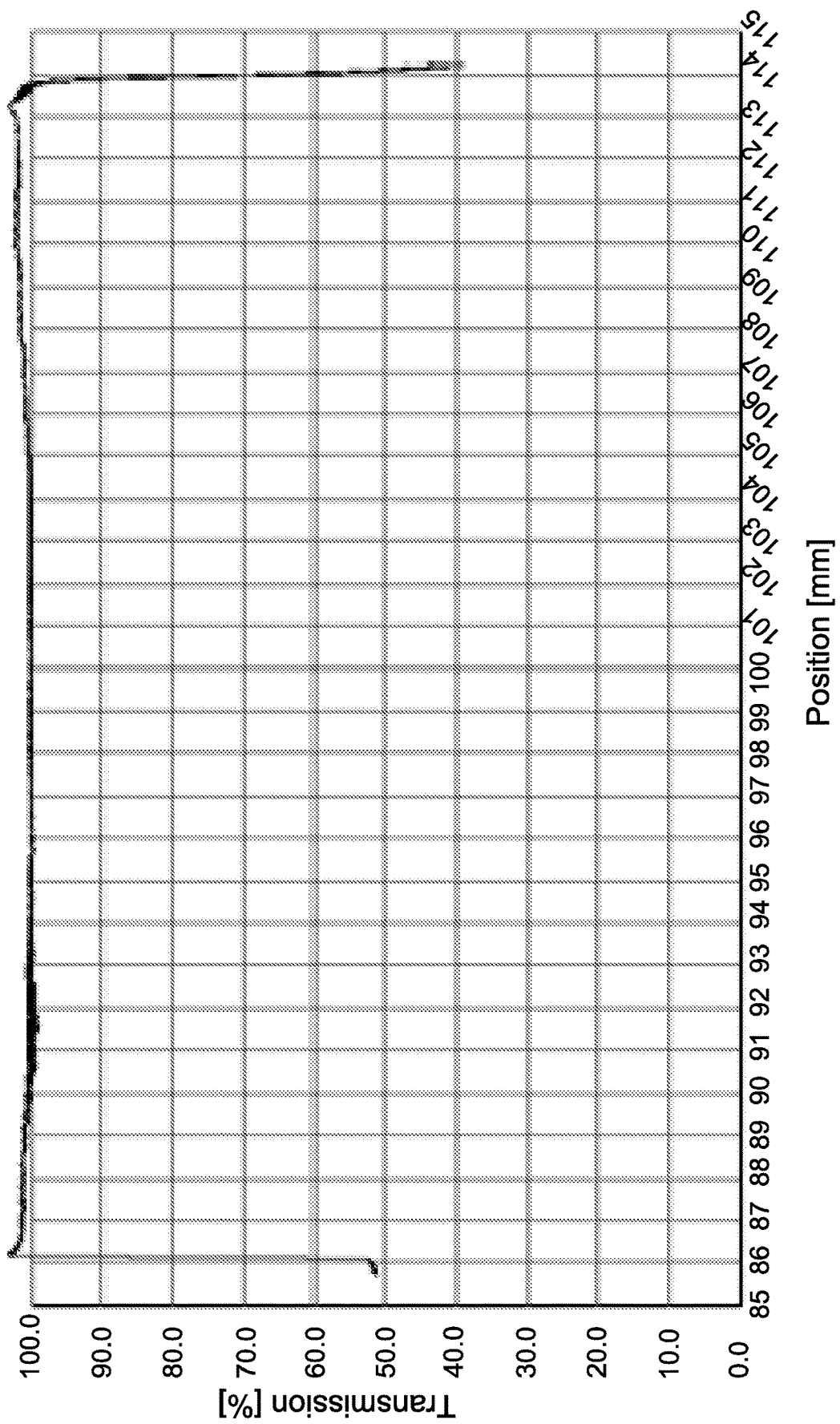
Figure 6C:
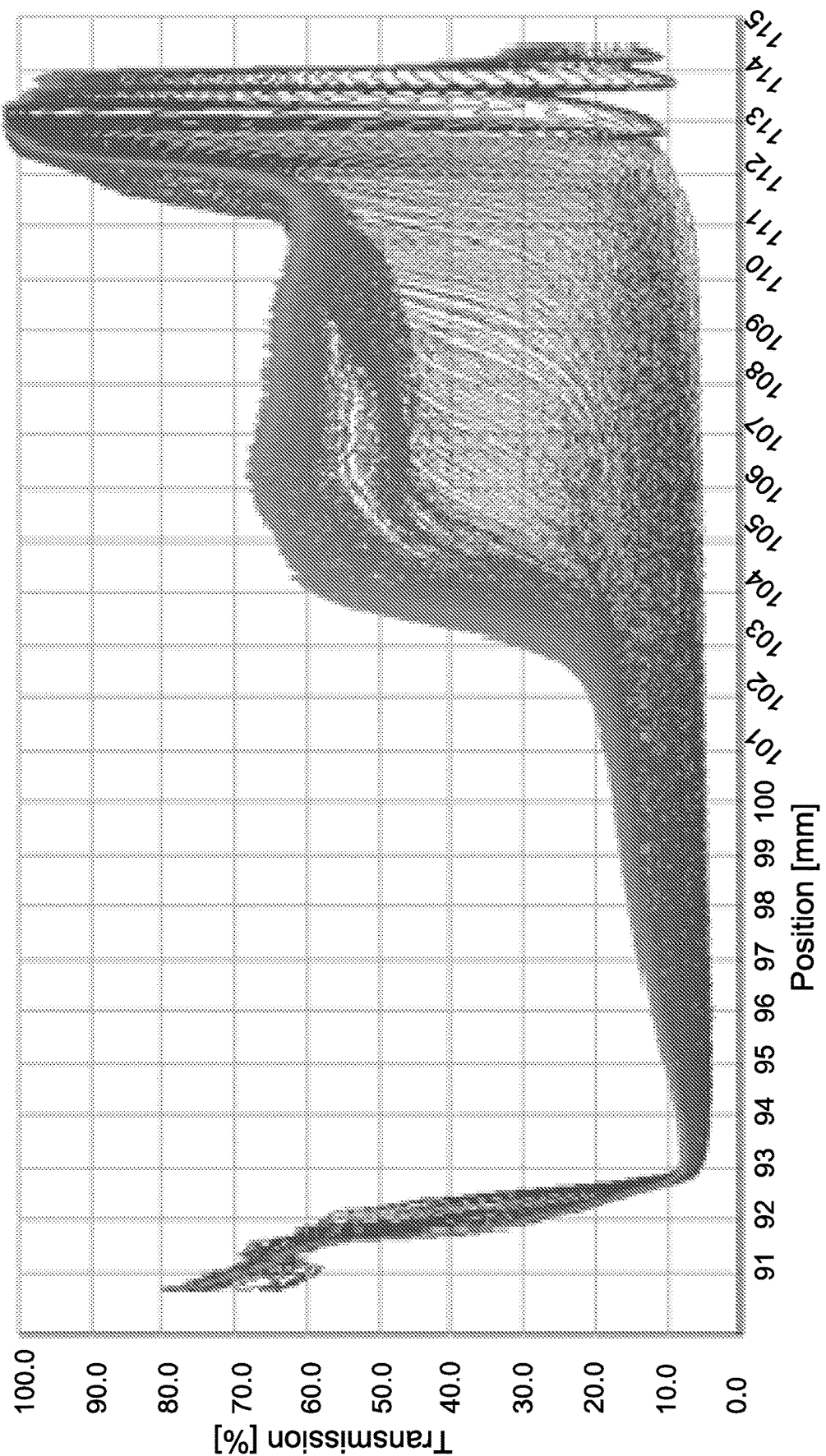

FIGS. 6A-6C show the change in sample transmission as a function of time. As seen, in both AX-1 formulations (concentrate and diluted form) the samples were stable through the whole analysis time, showing no changes in transmission (FIGS. 6A, 6B respectively). The 'Plus CBD' product showed phase separation already in early stage of measurements (FIG. 6C), with significant sediments.

Thus, while the CBD in an oil formulation was not stable and is predicted to separate and segregate over time, the formulations of this disclosure are stable at 3000 rpm and even after 17 hours of centrifugation. These conditions simulate minimum 2 years of storage.

In-Vivo Studies

Paw Withdrawal Test

Response to pain and anti-inflammatory activity in mice of the CBD-loaded formulations of this disclosure were assessed by oral administration of 5CS formulation loaded with 5 wt % CBD compared to CBD dispersed in olive oil.

Figure 7:
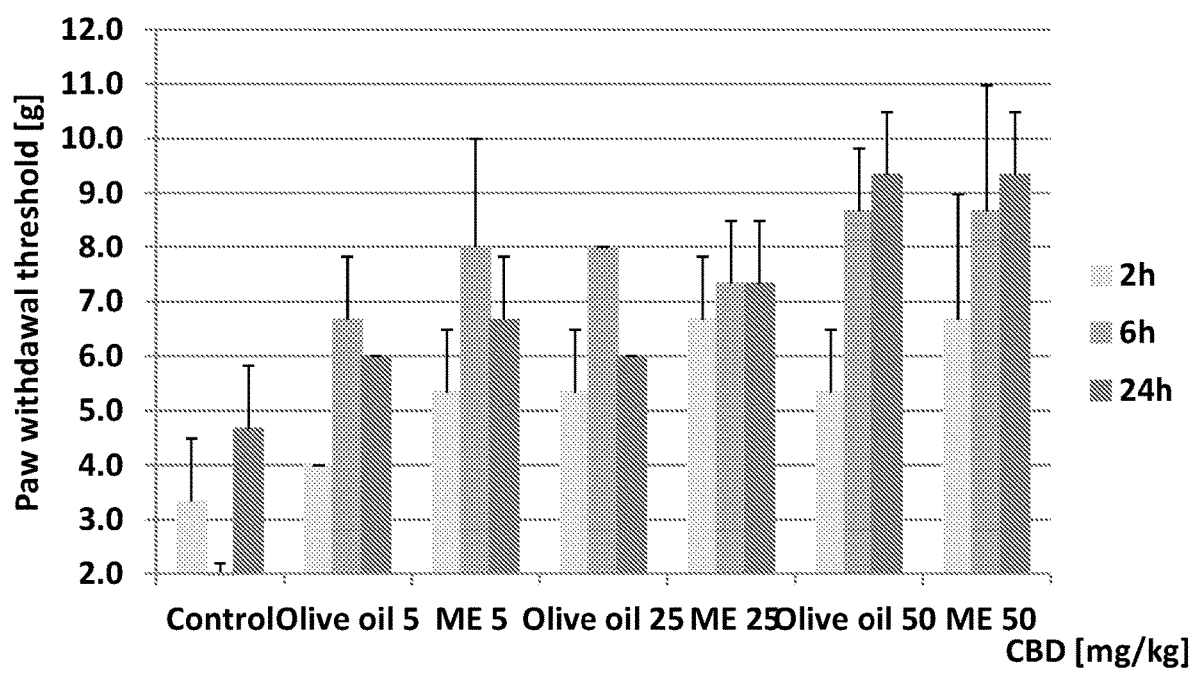
FIG. 7 shows the paw-withdrawal threshold in mice for 5 wt % crystalline CBD solubilized in 5CS formulation compared to crystalline CBD with the same concentration dispersed in olive oil.
Figure 8:
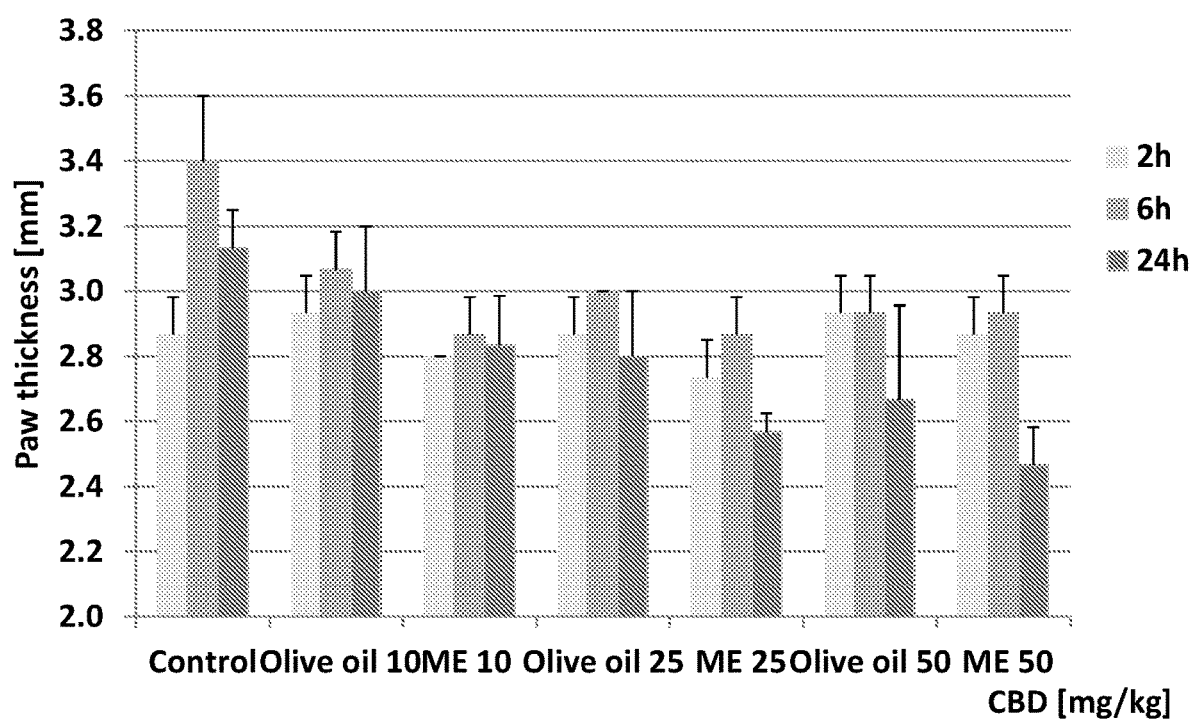
FIG. 8 shows the paw-thickness of inflammated paw in mice for 5 wt % crystalline CBD solubilized in 5CS formulation compared to crystalline CBD with the same concentration dispersed in olive oil.
Figure 9:
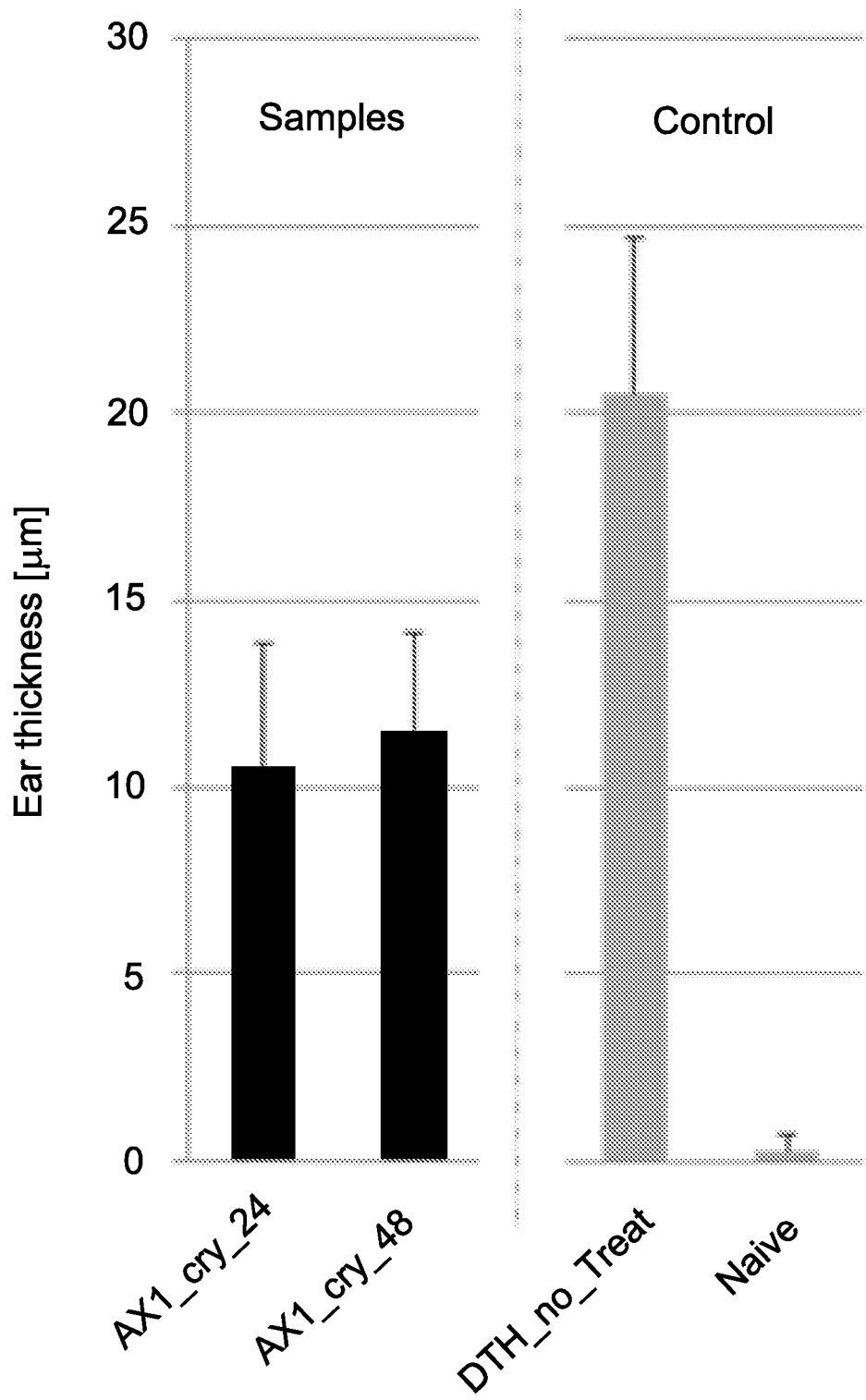
FIG. 9 shows the measured ear thickness of DHT-induced rats 24 hours after treatment.

Various doses of CBD were administered in the range of 5, 10, 25 and 50 mg/kg per dose. Paw-withdrawal was assessed by pricking the paw of the mice at varying loads and recording the withdrawal reflex response. FIG. 7 shows the paw-withdrawal threshold in mice for 5%-CBD 5CS formulation compared to CBD in olive oil. FIG. 8 shows the paw-thickness of inflammated paw in mice for 5%-CBD 5CS formulation compared to CBD olive oil extract.

As seen from FIG. 7, in all dosages tested, mice administered with the CBD-loaded formulation of the present disclosure showed higher tolerance to pain immediately after administration (2 and 24 hours), and at least comparable tolerance to pain to that in the oil-samples for a period of 6 hours from administration. This attests to the improved release, permeation and performance of CBD in the system after administration.

Further, as seen in FIG. 8, mice administered with the formulation of the present disclosure showed a more significant reduction in paw thickness in all dosages tested as compared to identical dosages of CBD in olive oil. Namely, the formulations of the present disclosure have an improved anti-inflammatory activity as compared to standard CBD in oil.

Delayed-Type Hypersensitivity (DTH)

CBD was shown to reduce inflammation response and pain-effected by inflammatory reaction. Without wishing to be bound by theory, inflammation reduction is achieved by various mechanisms, including agonist and antagonist binding to CB1 receptors, adenosine receptors and other GPCRs, involving the reduction of inflammatory cytokines and chemokines levels, such as IL-2, IL-6, TNF-$\alpha$, MCP-1, etc.

The therapeutic effect of oral administration of CBD-loaded formulations of this disclosure as anti-inflammatory agents. The CBD effect was evaluated using rat model of inflammation—Delayed Type Hypersensitivity (DHT) model. In this test, the reduction in ear swelling after inflammation-induction following treatment was measured.

The belly of male rats (average weight 250 g) was shaved and challenged 10 times with 500 µl of 2% oxazolone (400 mg oxazolone dissolved in 16 ml acetone and 4 ml mineral oil). The next day (referred to herein as day 1), 500 µl of CBD formulation oral treatment was given via gavage. On day 6, the ear thickness of the rats was measured using a caliper.

Rats were challenged with another dose of 50 µl of 0.5% oxazolone, and a second oral treatment of 500 µl CBD formulation was administered 2-hours after challenge. The ear thickness was measured again 12 and 24 hours after challenge, and blood samples were taken for serum preparation.

Samples composition: two doses were administered of crystalline CBD in AX-1 with a dose of 24 mg/kg BW and 48 mg/Kg BW (BW=Body Weight), compared to control of Naïve rats and rats with DTH-induction that were not given any treatment.

As seen in FIGS. 9 and 10A-D, a significant reduction in ear thickness and inflammatory appearance (redness and edema) as a result of the treatment with crystalline CBD solubilized in AX-1 was obtained compared to DTH-induced rats that were not treated. The anti-inflammatory effect of crystalline CBD solubilized in AX-1 is more significant than that seen for Ethanol extractions with both dose regiments. While the Naive rats showed no redness or swelling, the DTH-challenged rats that were not treated showed an inflammatory and swelling reaction. Rats treated with AX-1 showed relatively significant reduction in swelling and redness of the treated rats.

Pharmacokinetic Profile—1

The pharmacokinetics of the profile of CBD in the blood of rats after oral administration 5CS formulation was assessed in comparison to CBD dispersed in olive oil at various dosage of 10, 25, 50 mg CBD/kg body weight. 60 male rates (SD), weighing 230-250 g were randomly allocated into the study groups as shown in Table 6. Rats were administered orally via gavage with test formulations.

TABLE 6 pharmacokinetic test design

| Group | Number of rats | Formulation | Dose (mg/kg bw) | Regimen | Blood sampling (hr) |
|---|---|---|---|---|---|
| 1 | 5 | 5CS | 5 | PO | 0.5, 2, 4, 8, 12, 24 |
| 2 | 5 |  | 10 |  |  |
| 3 | 5 |  | 25 |  |  |
| 4 | 5 |  | 50 |  |  |
| 5 | 5 | In9(6) | 5 | PO | 0.5, 2, 4, 8, 12, 24 |
| 6 | 5 |  | 10 |  |  |
| 7 | 5 |  | 25 |  |  |
| 8 | 5 |  | 50 |  |  |
| 9 | 5 | Olive oil | 5 | PO | 0.5, 2, 4, 8, 12, 24 |
| 10 | 5 |  | 10 |  |  |
| 11 | 5 |  | 25 |  |  |
| 12 | 5 |  | 50 |  |  |

Figure 10A:
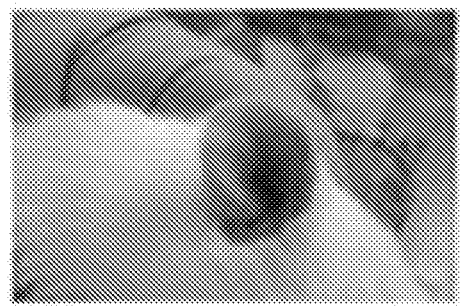
FIGS. 10A-D are pictures of rats' ears in DHT test: non-treated DHT-induced (FIG. 10A), and naïve rats (FIG. 10B), 24 mg/kg BW of 5CS formulation (FIG. 10C), 48 mg/kg BW of AX-1 formulation (FIG. 10D).
Figure 10B:
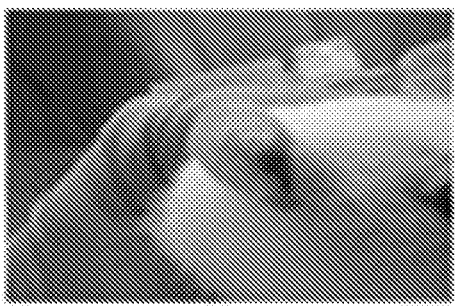
Figure 10C:
Figure 10D:
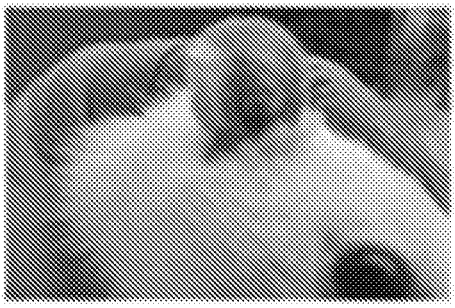
Figure 11A:
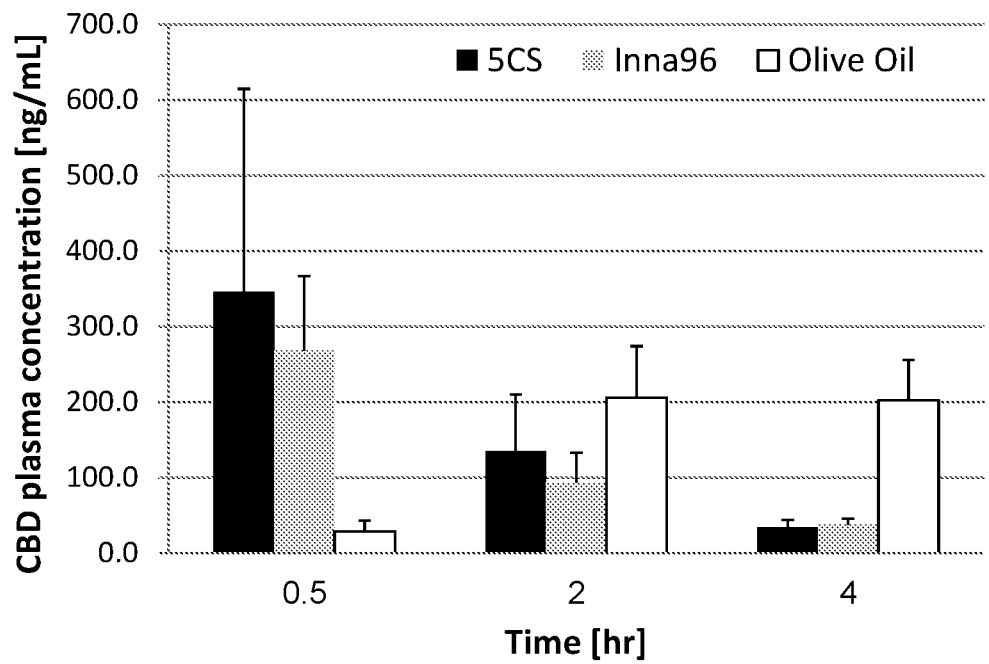
FIGS. 11A-11C shows the pharmacokinetics of the profile of CBD in the blood of rats after oral administration delivered form 5CS and In9(6) systems vs. CBD dispersed in olive oil at various dosage of 10, 25, 50 mg CBD/kg body weight, respectively.
Figure 11B:
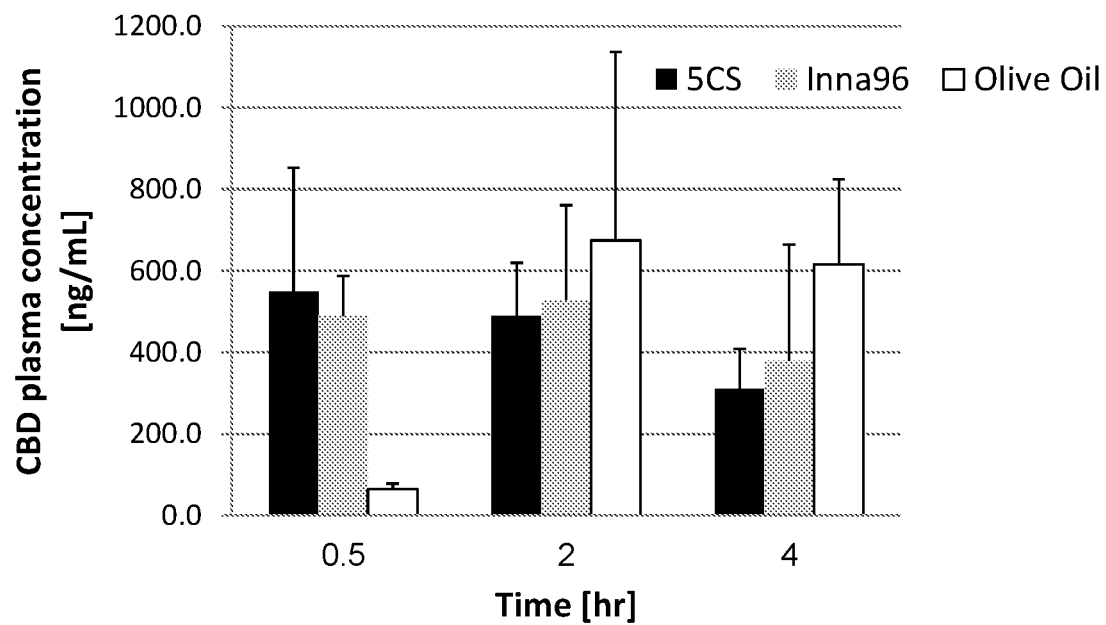
Figure 11C:
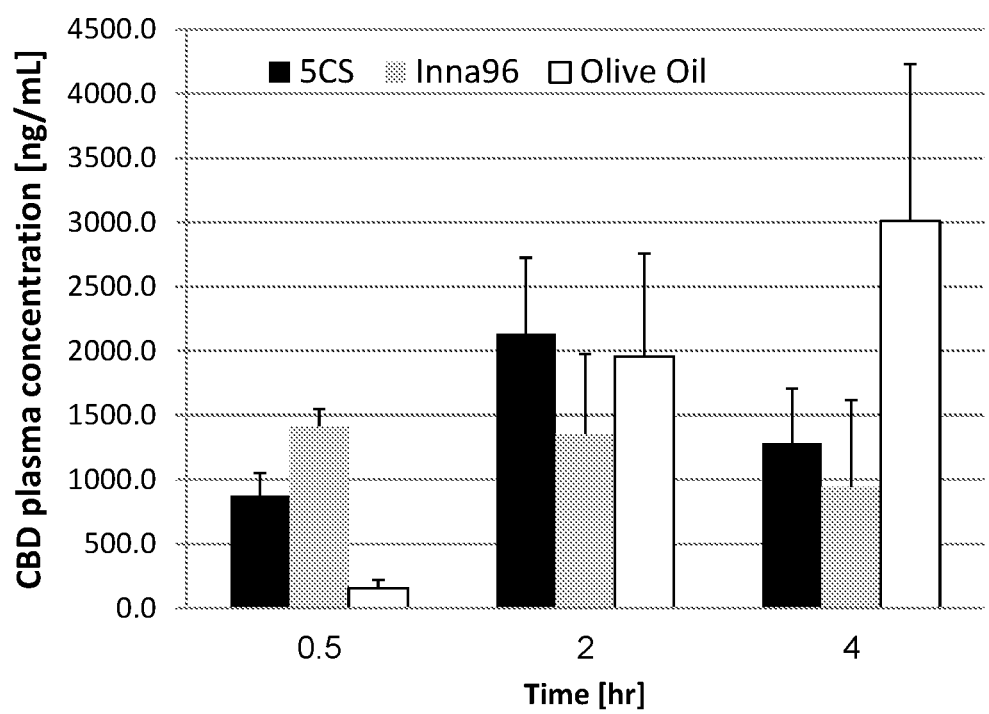

As can be seen from FIGS. 10A-10C, the CBD levels in the blood derived from formulation 5CS and In9(6) within half an hour after oral administration are by up to 16-fold higher than the levels obtained from oil dispersion. These results indicate a very fast absorption and high levels of permeation. After 4 hours the absorption of the CBD in oil reaches its maximum levels (Tmax). It can also be seen that a strong permeation is achieved with formulations of this disclosure with low level of CBD (10 mg/kg), while significantly higher dosage is required for obtaining the same level in the blood when CBD is dispersed in oil required.

Pharmacokinetic Profile—2

PK assessment for additional formulations were carried out for formulations detailed in Tables 7-1 and 7-2.

TABLE 7-1

Additional formulations for PK assessment

|  | Formulation AX-1 | | Formulation AX-1(B) | |
|---|---|---|---|---|
|  | Component | wt % | Component | wt % |
| Oil | Limonene | 5 | triacetin | 5 |
| Hydrophilic surfactant | Polysorbate 80 (Tween 80) | 45 | Polysorbate 80 (Tween 80) | 45 |
| Co-surfactant | Propylene glycol (PG) | 45 | Propylene glycol (PG) | 45 |

TABLE 7-1-continued

Additional formulations for PK assessment

| | Formulation AX-1 | | Formulation AX-1(B) | |
|---|---|---|---|---|
| Component | | wt % | Component | wt % |
| Solvent | Ethanol | 5 | — | — |
| Phospholipid | — | — | Phosphatidylcholine | 5 |

TABLE 7-2

Additional formulations for PK assessment

| | Formulation OR103(2) slow release | | Formulation OR210SE | |
|---|---|---|---|---|
| | Component | wt % | Component | wt % |
| Oil | Triacetin | 5 | MCT | 5 |
| Hydrophilic surfactant | Labrasol | 25 | L-1695- sucrose mono/dilaurate | 60 |
| | Cremophor EL castor oil* | 35 | | |
| Co-surfactant | Propylene glycol (PG) | 20 | Propylene glycol (PG) | 20 |
| Solvent | Isopropyl alcohol | 5 | Isopropyl alcohol | 5 |
| Phospholipid | Phosal 50 PG** | 10 | Phosal 50 PG** | 10 |

Figure 12A:
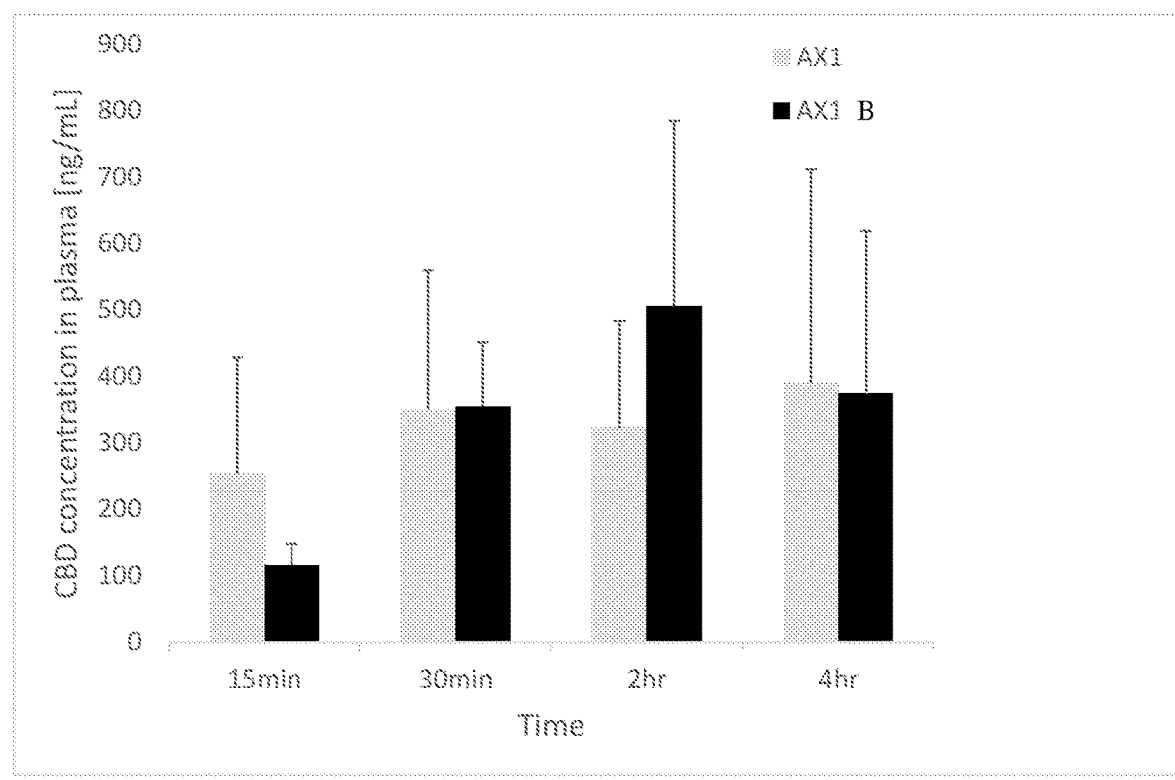
FIGS. 12A-12B shows the pharmacokinetics of the profile of CBD in the blood of rats after oral administration of: AX-1 compared to AX-1(B) (FIG. 12A), and AX-1, 5CS, OR201SE and OR103 (FIG. 12B).

*Polyoxyl 35 castor oil
**Phosal 50 PG composed of 1.5-2.5% wt ethanol, >500 ppm ethylenemethylketone, 0.5 wt % water, 33.8-41.2 wt % propylene glycol, <50.0 wt % phosphatidylcholine, >6 wt % lyso-phosphatidylcholine PK study in rats was carried out to measure the levels of CBD in the bloodstream after oral administration of 25 mg/kg BW (Body Weight) comparing formulations: AX-1 original to AX-1(B). The PK profile of CBD showed similar kinetics for both formulations, as can be seen in FIG. 12A. Therefore, one can replace D-limonene and EtOH by components which are less bitter and are still pharmacologically permitted for administration to improve patient compliance.

Similarly, PK study in rats was carried out to measure the levels of CBD in the bloodstream after oral administration of 25 mg/kg BW given OR210SE or OR103(2) compared to 5CS and AX-1.

Figure 12B:
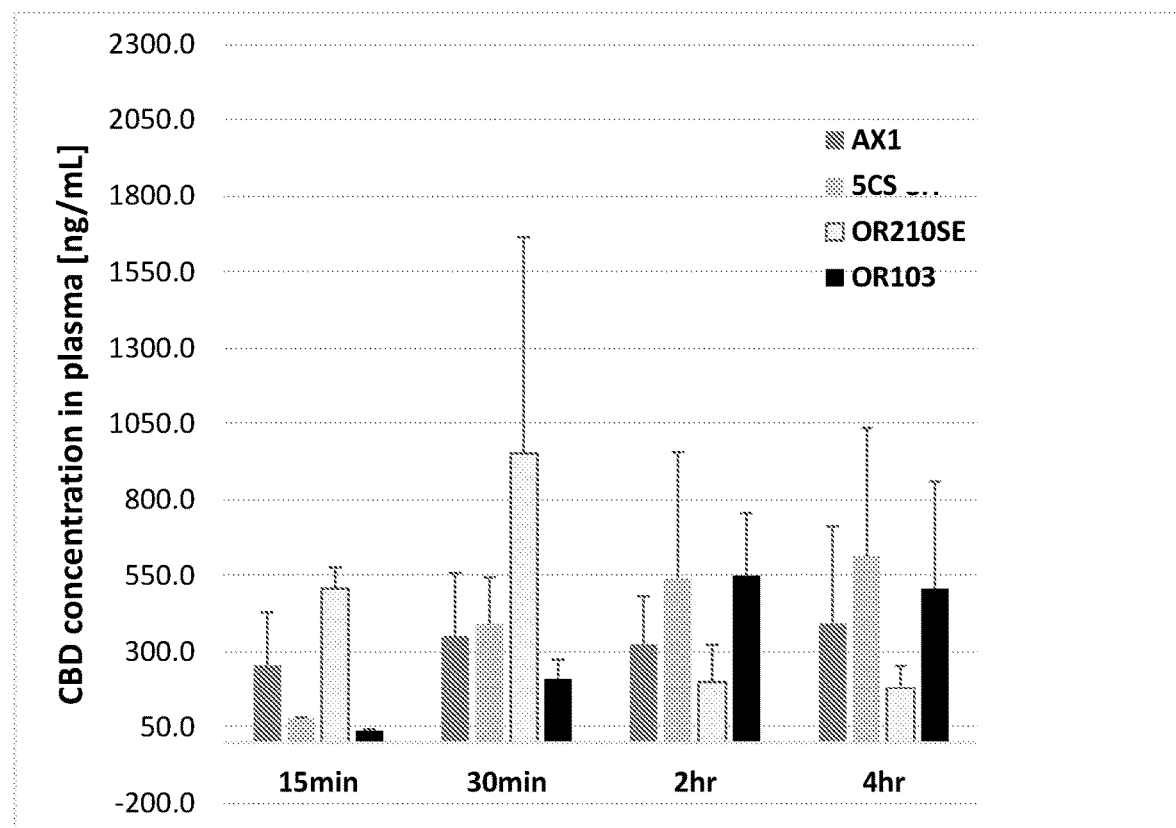

As seen in FIG. 12B, OR210SE shows a better PK profile, absorbing much higher levels of CBD to the blood stream after oral administration compared to AX-1 and 5CS formulation (all were administered in their concentrated form). The Cmax after administrating OR210SE was observed at 30 min with relatively high concentration compared to AX-1 (~900 ng/mL vs. 550 ng/mL respectively). Formulation OR103(2) exhibits a more delayed absorption of CBD with a Cmax of between 2-4 hr from administration. This formulation also shows relatively high levels of CBD reaching the bloodstream. OR103(2) and OR210SE may thus be suitable for delayed release formulations.

Stability of CBD in Stimulated Gastric Fluid (SGF)

Since oral administration of CBD is known to showed incidents of side effects that might be contributed to the degradation of CBD to THC with the exposer to gastric fluid, CBD stability was tested at simulating gastric fluid environment when solubilized in AX(1) and 5CS.

Stock solutions of 3% CBD in MeOH, AX1 and 5CS were prepared. A medium of stimulating gastric fluid (SGF) was prepared by dissolving sodium chloride (0.2 w/v %) and hydrochloric acid (0.1M) in DDW, and incubated at 37° C.

For MeOH solution sodium dodecyl sulfate (1 w/v %) was added to the SGF. 500 ml of SGF mediums was contained in an appropriate Erlenmeyer flask. At time 0-1 ml of each CBD stock solution was added to the SGF. The mixture was vigorously shaken at a water bath warmed to 37° C. and immediately 1 ml of the solution was sampled and replaced with an equal volume of preheated SGF medium. Similarly, same volume was sampled at 5, 10, 15, 20, 30, 45, 60, 75, 90, 120, 150 and 180 minutes. Each 1 mL sample was immediately neutralized to a pH of 7 to 9, with 980 µL of 0.1M sodium hydroxide solution and 3 ml MeOH, and pH levels were tested. All samples were kept at 4° C. until HPLC analysis.

For MeOH solution and AX1 system additional samples were taken every 30 min and injected directly into the HPLC without further treatment. This was to determine that naturalization do not affect the profile seen. The measured CBD concentration was divided to the initial concentration ($C/C_0$) at each time point.

Figure 13A:
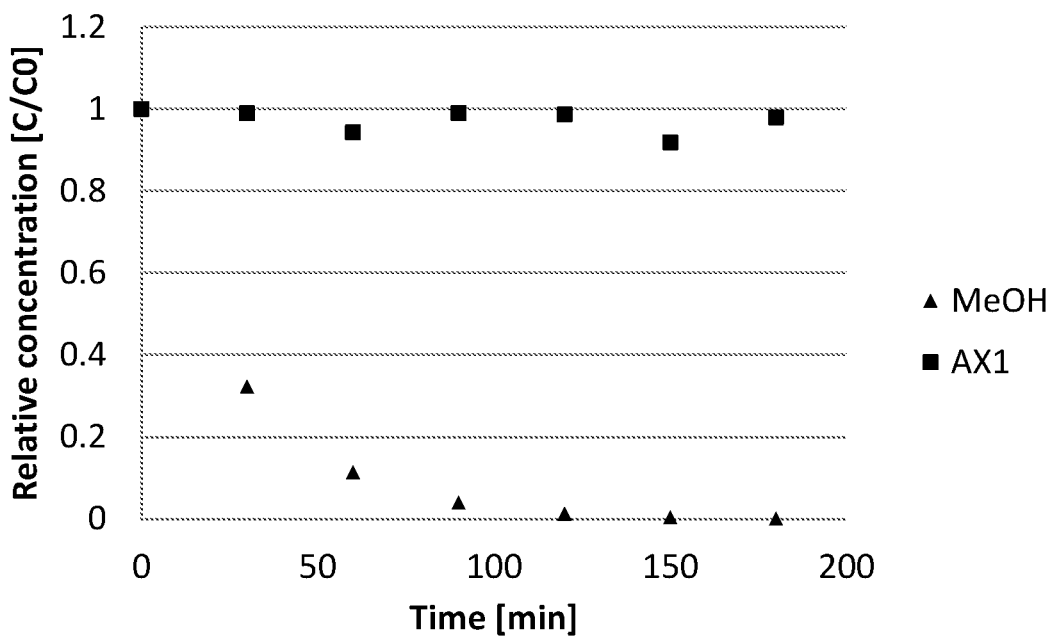
FIGS. 13A-13B show relative changes in CBD concentration as a function of time while incorporate in AX1 and MeOH, and CBD content within simulated gastric fluid (SGF) as a function of time while solubilized within MeOH, 5CS and AX1, respectively.
Figure 13B:
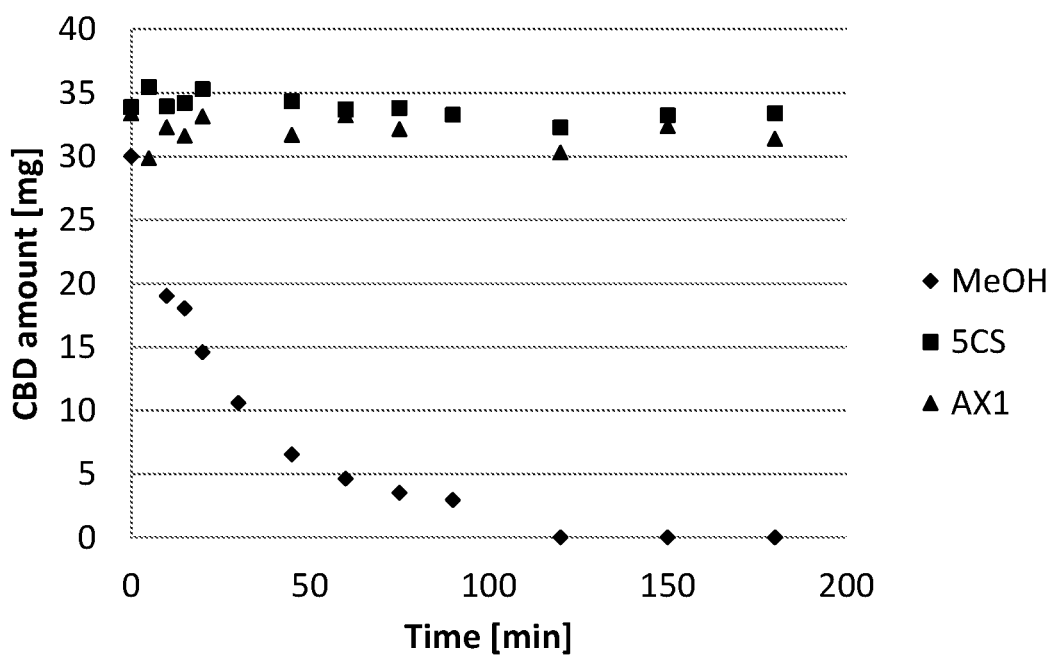

FIGS. 13A-13B show the changes in CBD content as a function of time in both neutralized and non-neutralized samples. CBD in MeOH as a suspending medium showed significant degradation over time. Degradation had begun very fast, starting already after 5 minutes. Within 30 min 68% of the molecule decomposes, and after 2 hours less than 4% CBD were left. The decomposition of the CBD had resulted in 7 peaks detected using HPLC-UV analysis. 4 unknown peaks, termed 'Unk' and three peaks were identified as $\Delta^8$-THC, $\Delta^9$-THC and CBN. However, when CBD was loaded within both 5CS and AX1 no degradation was observed ($C/C_0$ remained 1). CBD levels were stable and constant, showing no decomposition products, even after 3 hours of measurements. The samples that were measured after neutralization or immediately after sampling showed similar results, indicating the accuracy of the method.

According to previous reports, at acidic environment CBD decomposes mainly to THC and some additional minor related cannabinoids. HPLC analysis showed a total of 7 degradation products, including $\Delta^9$-THC, $\Delta^8$-THC and CBN, detected at different times.

Figure 13C:
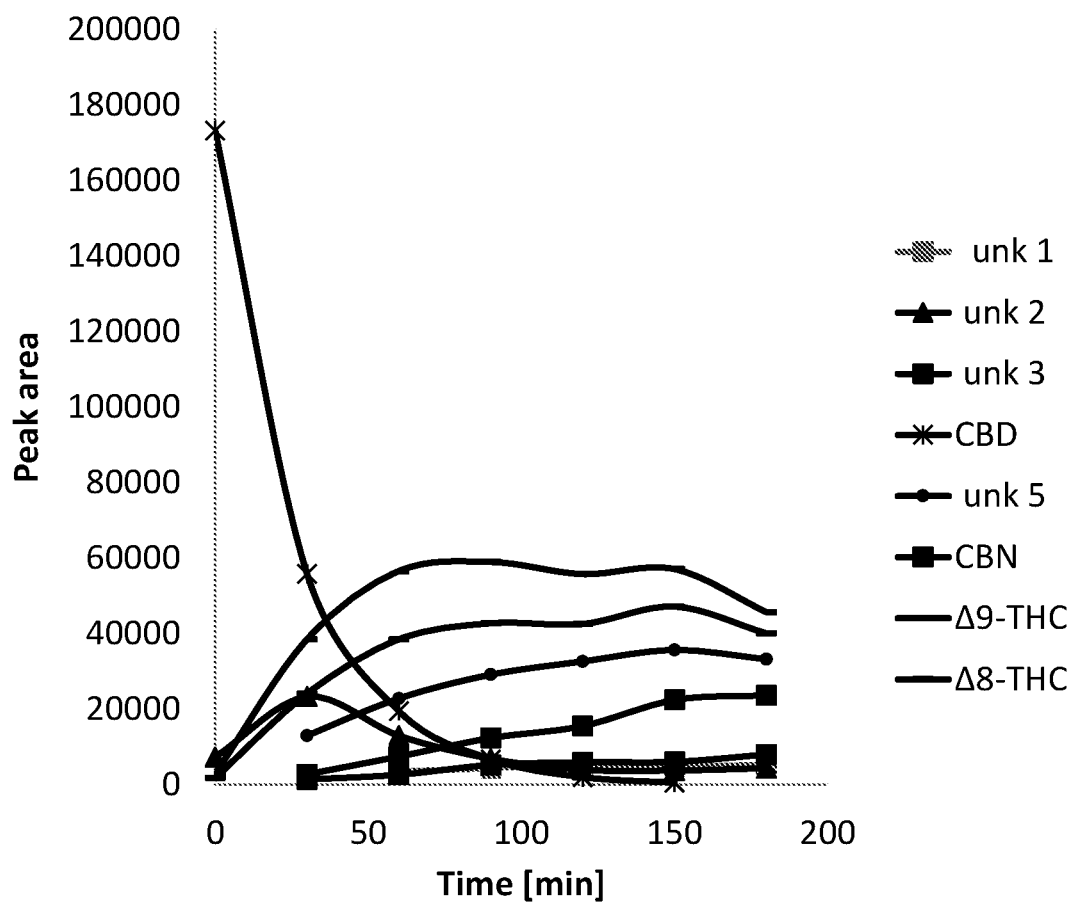
FIG. 13C shows cannabinoids degradation as a function of time within simulated gastric fluid (SGF).

The trend of the descending CBD peak area is shown in FIG. 13C. Simultaneously the peaks area of related degradation products increases, even though it seems some of them also decomposed (compound "unk 2") within time, while other starts to rise at that time point ('unk 5' and 'unk 3').

From the results, it is concluded that administration of CBD in methanol is expected to result in very fast transformation of CBD into THC due to the acidic environment, which is may lead to undesired psychoactive adverse effects. In contract, the CBD solubilized in the 5CS and In9(6) systems is well protected against transformation to THC even after 180 minutes after exposure to the acidic gastric fluid.

Figure 14A:
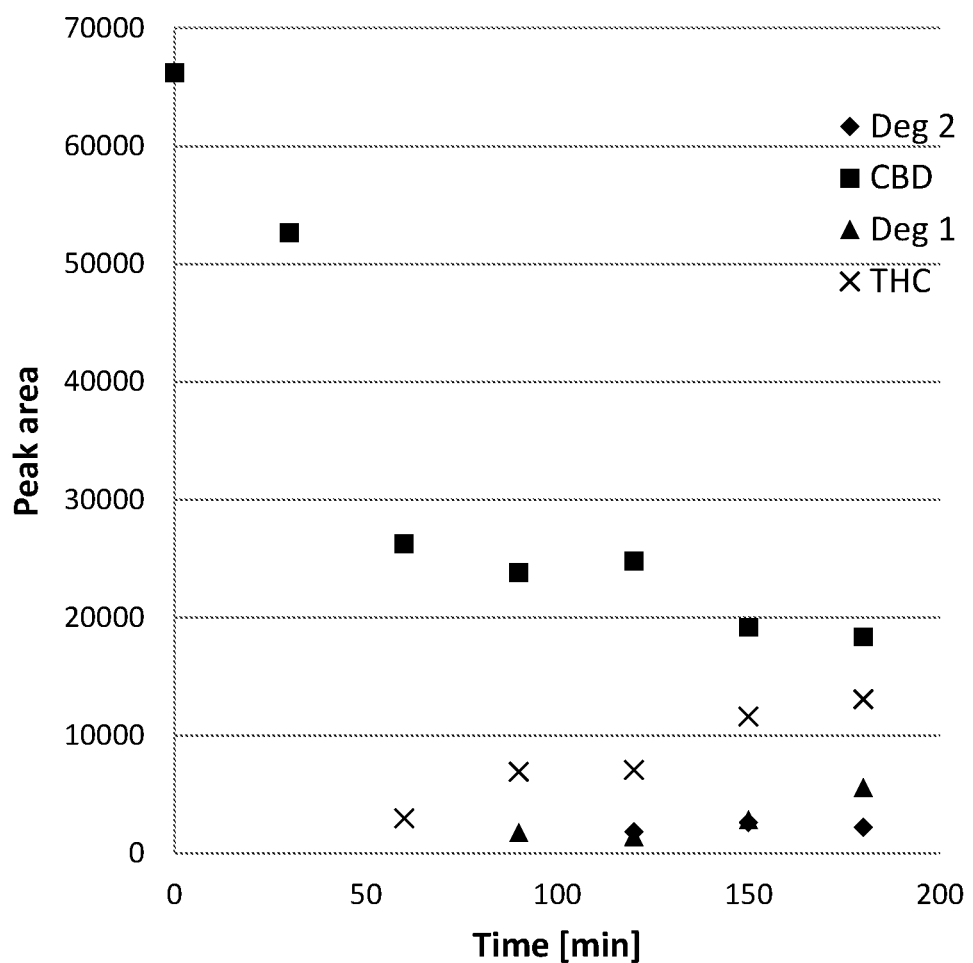
FIGS. 14A-14B show cannabinoid degradation as a function of time within simulated gastric fluid (SGF) of the commercial product RSHO™ (FIG. 14A) and CBD in olive oil (FIG. 14B).
Figure 14B:
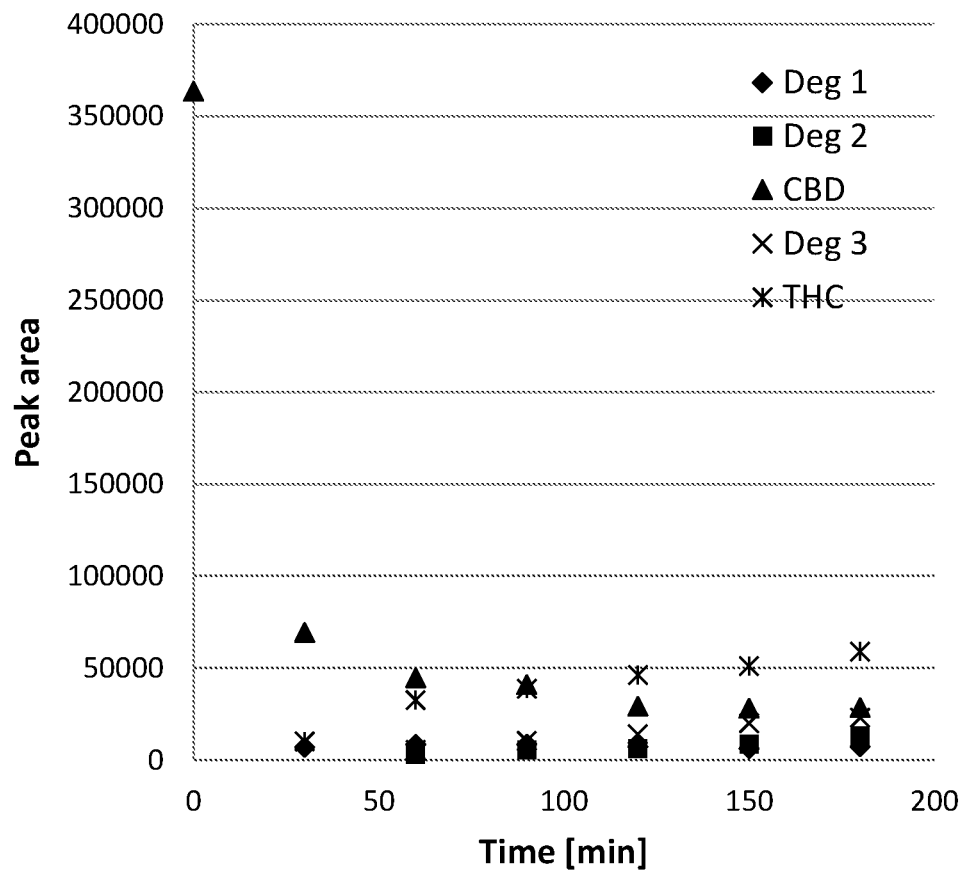

In comparison, the CBD profile in SGF with a commercial product ('RSHO'™—containing CBD dissolved in vegetable oil) and CBD dissolved in pure olive oil were evaluated. RSHO profile of degradation in SGF is shown in FIG. 14A, while FIG. 14B shows the CBD in olive oil profile of degradation in SGF.

As opposed to AX-1 and 5CS in which CBD remains stable when exposed to SGF for 180 min, the CBD in the commercial product or in olive oil degrades relatively fast within 30 min after exposure. Thus, the formulations described herein provide a 'protective shield' for CBD to be absorbed directly when administrated orally into the bloodstream, and not its degradation products, such as THC or other cannabinoids.

Compounding

Lyophilization and Resuspension

CBD-loaded formulations 5CS and AX-1 were compounded for lyophilization as detailed below.

Concentrate samples of 2.5 wt % CBD-loaded AX1 and 5 wt % CBD-loaded 5CS formulations were diluted (10 times) with the following solutions:

Dextrin (10-20 w/v %)
Lactose (10-20 w/v %)
Mannitol (10-20 w/v %)
Maltodextrin (10-20 w/v %)
Erythritol (10-30 w/v %)
Sorbitol (20-70 w/v %)

Figure 15A:
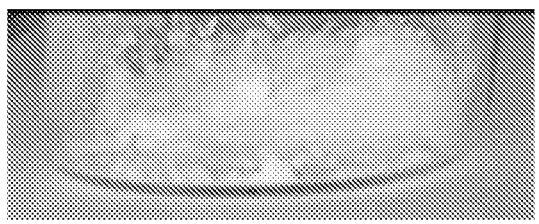
FIGS. 15A-15B show samples of 5 wt % CBD-loaded 5CS after compounding with mannitol solution at lyophilized state (FIG. 15A) and reconstituted state (FIG. 15B).

The diluted samples were frozen by liquid nitrogen and lyophilized for at least 24 hr. After freeze-drying, powder of solid particles was obtained (FIG. 15A).

Figure 15B:
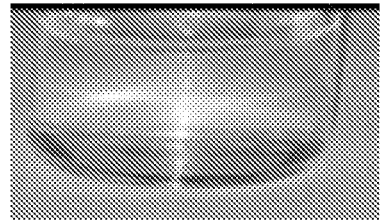

Next, the CBD loaded particles were re-dispersed in water (10-90% WT) to give the reconstructed microemulsion (FIG. 15B). The formulations had completely regained their original transparent homogeneous appearance, showing no phase separation or precipitation of the CBD.

In order to determine if the nano-sized droplets had retained their structure and size, reconstituted powder of 5CS diluted with mannitol was measured for its droplet size via DLS instrument, as shown in Table 8.

TABLE 8

Droplet size before lyophilization and after reconstitution

| Water content (wt %) | Before lyophilization (Z-average; nm) | After lyophilization and reconstitution (Z-average; nm) |
|---|---|---|
| 70 | 11.6 | 12.01 |
| 80 | 10.3 | 10.8 |
| 90 | 10.2 | 10.4 |

Similar droplet size was observed seen before lyophilization (original formulation) and after reconstitution with different water ratios.

Figure 16A:
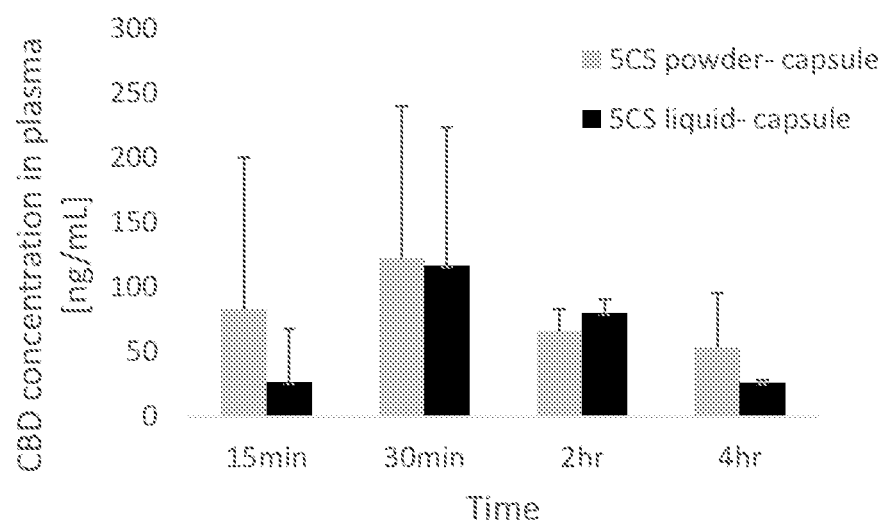
FIG. 16A shows PK profiles of 5 wt % CBD-loaded 5CS in original microemulsion form compared to lyophilized powder.

The lyophilized powder was introduced into capsules customized in their size for oral administration in rats (TROPAC CAPSULES). The CBD in the bloodstream was evaluated after oral administration compared to the liquid concentrate formulation with the same dose of 10 mg/kg BW. The PK profile of the lyophilized powder and that of the liquid concentrate formulation was similar, as shown in FIG. 16A, showing no effect of the freeze-drying of 5CS to powder, as was foreseen by the DLS results.

Figure 16B:
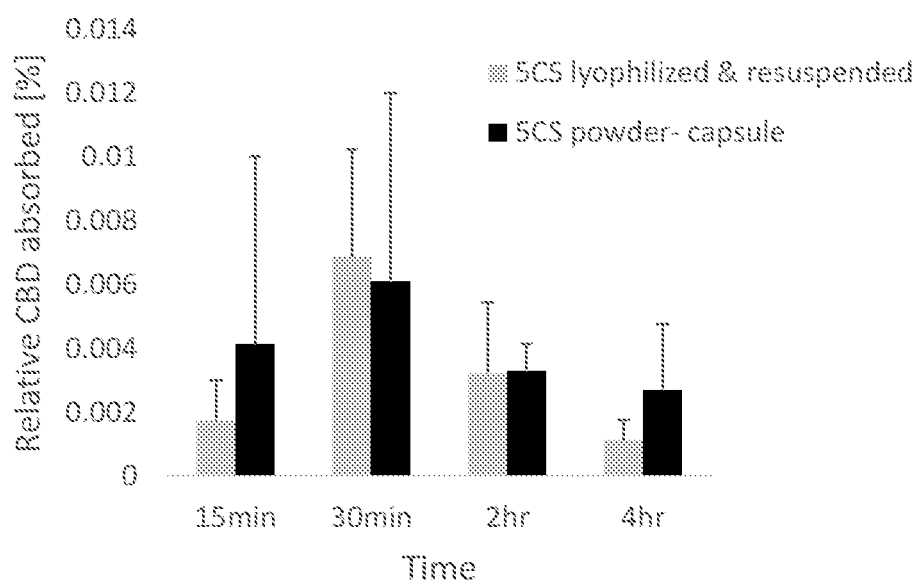
FIG. 16B shows PK profiles of 5 wt % CBD-loaded 5CS in original microemulsion form compared to reconstituted lyophilized powder.

Moreover, the lyophilized powder and its reconstituted sample results in a similar kinetic profile and CBD amount reaching the blood stream (FIG. 16B). This result indicates that there is no effect on the performance and/or bioavailability of the CBD by hydration of the powder.

As lyophilization and reconstitution did not hinder from the properties of the formulation, it is possible to administer the formulation either in powder or in liquid form, depending on the end-user/patient preference.

Co-Solubilization with Other Active Components

Docohexanoic acid (DHA):

DHA is an omega-3 fatty acid naturally found throughout the body and is most abundant in the cerebral cortex, retina and heart. Therefore, DHA is essential for the growth and functional development of the brain, showing improvements in learning ability, cognitive behavior and reduced depression. Decrease in DHA consumption is associated with cognitive decline during aging and with onset of sporadic Alzheimer disease.

In addition, DHA is known to help reduce triglycerides in the blood, decreasing thrombosis and preventing cardiac arrhythmias. Epidemiological studies have shown a strong correlation between fish consumption with high concentration of DHA and reduction in sudden death from myocardial infarction.

The opposite effects of DHA are also seen and studied with inflammation, particularly with rheumatoid arthritis (RA), and with asthma. DHA has a positive effect on diseases such as hypertension, arthritis, atherosclerosis, depression, adult-onset diabetes mellitus, myocardial infarction, thrombosis, and some cancers.

It can mainly be obtained from our diet including fish oil or algae, but has very limited bioavailability and therefore should be consumed in high levels and intensity to reach sufficient levels in the body.

Solubilizing CBD and DHA is not an easy task. Using 5CS and AX-1 formulations, a relatively high concentration of both CBD and DHA in 1:1 ratio (50 mg/mL CBD and 50 mg/mL DHA and higher) was achieved, resulting in a transparent, stable formulation with nano-sized droplets. This system, although "carrying" a very large amount of total active molecules was still fully dilutable. The system can solubilize any desired ratio of CBD:DHA. This dual molecule system can result in a multifunctional therapeutic effect. Moreover, the DHA added to the composition, being a poly-unsaturated long fatty acid, may act as a bioavailability enhancer improving the delivery CBD.

Curcumin:

Curcumin is a small molecule that is the prototypical 'curcuminoid' having similar effects to other polyphenols. It is known as a very potent anti-inflammatory, anti-cancer molecule. It has also been demonstrated as a molecule that helps reduce cognitive decline associated with aging, reduce lipid and plaque levels in arteries and reduce the risk of diabetes. However, it has a very poor oral bioavailability. Combining both CBD and curcumin can have an increase effect on the reduction of inflammation and additional dual beneficial therapeutics affect. Both curcumin and CBD were successfully co-solubilize in 5CS formulation at a concentration of 60 mg/mL CBD and 50 mg/mL curcumin, and 50 mg/mL CBD and 15 mg/mL curcumin in AX-1 formulation. The resulting formulation with both active molecules are transparent with an orange appearance (curcumin coloring effect) showing no phase separation or precipitation.

Flavoring 2.5% CBD-loaded formulations were tested for the possibility to add flavoring agents, such as mint, tea w/lemon, tropical, citrus, cranberry-pomegranate. The diluted formulations were transparent and stable after preparation.

Further, AX1 samples were prepared with monk fruit (*Siraitia grosvenorii*) powder and monk fruit juice and flavors (oil base and water base). Both monk fruit powder and monk fruit juice were compatible with AX1 concentrate. In case of flavors, the addition of oil-based flavors resulted in phase separation in contrast to water-based flavors which kept the samples transparent and stable.

For 5CS, samples were prepared with monk fruit powder and monk fruit juice and flavors (oil base and water base). Only monk fruit powder resulted in stable systems, however in order to completely dissolve the powder extra PG was added (10% of final product). Both water-based and oil-based flavors were compatible.

Thus, addition of flavoring and other additives does not adversely affect the formulation, allowing to mask the bitter taste in both diluted and concentrated forms.

Encapsulating into Soft Gel Capsules

To permit another form of oral administration, 5CS formulation was encapsulated in soft gel capsules. The soft gels were found to be intact after long storage without showing any leakage or damage to the coating, resulting in no weight loss or humidity in the bottle.

The invention claimed is:

1. A cannabinoid-loaded formulation, comprising:
   at least one oil comprising medium chain triglycerides (MCT), the oil being in an amount of between about 0.5 wt % and 10 wt %,
   at least one hydrophilic surfactant in an amount of between about 30 and about 85 wt %, said at least one hydrophilic surfactant is selected from the group consisting of polyoxyethylene sorbitan monolaurate, polyoxyethylene sorbitan monopalmitate, polyoxyethylene sorbitan monooleate, polyoxyethylene esters of saturated and unsaturated castor oil, ethoxylated monoglycerol esters, ethoxylated fatty acids, and combinations thereof,
   at least one co-surfactant in an amount of between about 1 wt % and about 50 wt %, the ratio between the at least one hydrophilic surfactant and the at least one co-surfactant is between about 1:1 and 6:1 (wt/wt), said at least one co-surfactant is selected from the group consisting of polyols, diglycerides, polyglyceryl-3 dioleate, phospholipids, polyoxyethylenes, and combinations thereof,
   at least one solvent in an amount of between 0 wt % and 15 wt %, and
   at least one cannabinoid in an amount of between about 0.1 wt % and about 12 wt %, said at least one cannabinoid is selected from the group consisting of cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CDB), cannabidiol monomethylether (CBDM), cannabidiol-$C_4$ (CBD-$C_4$), cannabidivarinic acid (CBDVA), cannabidiorcol (CBD-$C_1$), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid-$C_4$ (THCA-$C_4$), delta-9-tetrahydrocannabinol-$C_4$ (THCA-$C_4$), delta-9-tetrahydrocannabivarinic acid (THCVA), delta-9-tetrahydrocannabivarin (THCV), delta-9-tetrahydrocannabiorcolic acid (THCA-$C_1$), delta-9-tetrahydrocannabiorcol (THC-$C_1$), delta-7-cis-isotetrahydrocannabivarin, delta-8-tetrahydrocannabinolic acid A ($\Delta^8$-THCA), delta-8-tetrahydrocannabinol ($\Delta^8$-THC), cannabicyclolic acid (CBLA), cannabicyclol (CBL), cannabicyclovarin (CBLV), cannabielsoic acid A (CBEA-A), cannabielsoic acid B (CBEAB), cannabielsoin (CBE), cannabinolic acid (CBNA), cannabinol (CBN), cannabinol methylether (CBNM), cannabinol-$C_4$ (CBN-$C_4$), cannabivarin (CBV), cannabinol-$C_2$ (CBNC2), cannabiorcol (CBN-$C_1$), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cistetrahydrocannabinol (cis-THC), 3,4,5,6-tetrahtdro-7-hydroxy-$\alpha$-$\alpha$-2-trimethyl-9-n-propyl-2,6-methano-2H-1-benzoxocin-5-methanol (OH-iso-HHCV), cannabiripsol (CBR), trihydroxy-delta-9-tetrahydroxycannabinol (triOH-THC), and any combination thereof;
   the formulation being in form of a water-free microemulsion having a droplet size of between about 5 nm and about 100 nm, and being fully dilutable by an aqueous diluent.

2. The cannabinoid-loaded formulation of claim 1, further comprising at least one additional oil, different from MCI, the at least one additional oil is selected from the group consisting of mineral oil, paraffinic oils, vegetable oils, glycerides, esters of fatty acids, liquid hydrocarbons and mixtures thereof.

3. The cannabinoid-loaded formulation of claim 2, wherein said at least one additional oil is selected from the group consisting of olive oil, soybean oil, canola oil, cotton oil, palmolein, sunflower oil, corn oil, rapeseed oil, grape seeds oil, hemp oil, pomegranate oil, avocado oil, peppermint oil, tomato oil, isopropyl myristate, oleyl lactate, coca caprylocaprate, hexyl laurate, oleyl amine, oleic acid, oleyl alcohol, linoleic acid, linoleyl alcohol, ethyl oleate, hexane, heptanes, nonane, decane, dodecane, D-limonene, neem oil, lavender oil, anise oil, rosemary oil, sage oil, hibiscus oil, menthol, capsaicin, grape seed oil, pumpkin oil, hemp oil, triglycerides or esters of fatty acids and mixtures thereof.

4. The cannabinoid-loaded formulation of claim 1, having a droplet size of between about 5 and about 30 nanometers.

5. The cannabinoid-loaded formulation of claim 1, wherein the formulation is capable of stabilizing the at least one cannabinoid in acidic environments.

6. The cannabinoid-loaded formulation of claim 5, wherein the acidic environment is gastric fluid.

7. The cannabinoid-loaded formulation of claim 6, wherein the at least one cannabinoid is cannabidiol (CBD), and wherein the formulation reduces the rate of transformation of the CBD into tetrahydrocannabinol (THC).

8. A pharmaceutical composition comprising the cannabinoid loaded-formulation of claim 1.

9. The pharmaceutical composition of claim 8, being in a form selected from a gel, a lotion, oil, soap, a spray, an emulsion, a cream, an ointment, capsules, soft-gel capsules, a patch, or a solution.

10. The pharmaceutical composition of claim 8, adapted for delivery of said cannabinoid topically, orally, by inhalation, nasally, transdermally, occularly or parenterally into the circulatory system of a subject.

11. The pharmaceutical composition of claim 8, further comprising a pharmaceutically acceptable carrier and/or a diluent.

* * * * *

UNITED STATES PATENT AND TRADEMARK OFFICE
CERTIFICATE OF CORRECTION

PATENT NO. : 11,819,490 B2
APPLICATION NO. : 16/338273
DATED : November 21, 2023
INVENTOR(S) : Nissim Garti et al.

It is certified that error appears in the above-identified patent and that said Letters Patent is hereby corrected as shown below:

In the Claims

Claim 2, Column 30, Line 21, "MCI" should read --MCT--.

Claim 3, Column 30, Line 31, "coca" should read --coco--.

Signed and Sealed this
Thirteenth Day of February, 2024

Katherine Kelly Vidal
*Director of the United States Patent and Trademark Office*